(12) United States Patent
Ahn et al.

(10) Patent No.: US 9,243,113 B2
(45) Date of Patent: Jan. 26, 2016

(54) SILICONE COMPOSITIONS COMPRISING A SWOLLEN SILICONE GEL

(75) Inventors: Dongchan Ahn, Midland, MI (US); William Schulz, Midland, MI (US); James Thompson, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 157 days.

(21) Appl. No.: 13/503,637

(22) PCT Filed: Oct. 19, 2010

(86) PCT No.: PCT/US2010/053112
§ 371 (c)(1),
(2), (4) Date: Apr. 23, 2012

(87) PCT Pub. No.: WO2011/049896
PCT Pub. Date: Apr. 28, 2011

(65) Prior Publication Data
US 2012/0219517 A1   Aug. 30, 2012

Related U.S. Application Data (60) Provisional application No. 61/254,476, filed on Oct. 23, 2009.

(51) Int. Cl.
| | | |
|---|---|---|
| C08G 77/442 | (2006.01) |
| A61K 8/04 | (2006.01) |
| A61K 8/893 | (2006.01) |
| A61Q 15/00 | (2006.01) |
| A61Q 19/00 | (2006.01) |
| C08L 83/10 | (2006.01) |

(52) U.S. Cl.
CPC .............. *C08G 77/442* (2013.01); *A61K 8/042* (2013.01); *A61K 8/893* (2013.01); *A61Q 15/00* (2013.01); *A61Q 19/00* (2013.01); *C08L 83/10* (2013.01); *A61K 2800/546* (2013.01)

(58) Field of Classification Search
None
See application file for complete search history.

(56) References Cited

U.S. PATENT DOCUMENTS

| | | | |
|---|---|---|---|
| 4,122,029 A | 10/1978 | Gee et al. | |
| 4,781,917 A | 11/1988 | Luebbe et al. | |
| 4,987,169 A | 1/1991 | Kuwata et al. | |
| 5,387,417 A | 2/1995 | Rentsch | |
| 5,760,116 A | 6/1998 | Kilgour et al. | |
| 5,811,487 A | 9/1998 | Schulz, Jr. et al. | |
| 5,919,441 A | 7/1999 | Mendolia et al. | |
| 5,981,680 A | 11/1999 | Petroff et al. | |
| 6,051,216 A | 4/2000 | Barr et al. | |
| 6,086,903 A | 7/2000 | Trinh et al. | |
| 6,346,583 B1 | 2/2002 | Kilgour et al. | |
| 6,444,745 B1 | 9/2002 | Kilgour et al. | |
| 6,531,540 B1 | 3/2003 | O'Brien | |
| 6,538,061 B2 | 3/2003 | Chaiyawat et al. | |
| 6,759,479 B2 | 7/2004 | O'Brien | |
| 6,770,708 B2 | 8/2004 | Kadlec et al. | |
| 7,019,098 B2 | 3/2006 | Hupfield | |
| 7,166,276 B2 | 1/2007 | Stephens et al. | |
| 7,649,068 B2 | 1/2010 | Ahn | |
| 7,732,543 B2 | 6/2010 | Loch et al. | |
| 7,850,870 B2 | 12/2010 | Ahn et al. | |
| 8,524,849 B2 | 9/2013 | Stark | |
| 2003/0072730 A1 | 4/2003 | Tournilhac | |
| 2003/0170188 A1 | 9/2003 | Ferrari et al. | |
| 2003/0235553 A1 | 12/2003 | Lu et al. | |
| 2004/0180032 A1 | 9/2004 | Manelski et al. | |
| 2004/0228821 A1 | 11/2004 | Sunkel et al. | |
| 2007/0298223 A1* | 12/2007 | Loch et al. ..................... 428/172 |
| 2008/0050552 A1 | 2/2008 | Ahn et al. | |
| 2008/0085983 A1 | 4/2008 | Ahn | |
| 2010/0022738 A1 | 1/2010 | Hashemzadeh | |
| 2011/0294958 A1 | 12/2011 | Ahn et al. | |
| 2012/0237464 A1 | 9/2012 | Ahn et al. | |

FOREIGN PATENT DOCUMENTS

| | | | |
|---|---|---|---|
| EP | 1266647 | 12/2002 | |
| EP | 1266648 | 12/2002 | |
| EP | 1266653 | 12/2002 | |
| GB | 2453952 | 4/2009 | |
| JP | H 06329736 | 11/1994 | ................ C08F 2/04 |
| JP | 07-82327 A | 3/1995 | |
| JP | 2001-131248 | 5/2001 | ............ C08F 290/06 |
| JP | 2001-294512 | 10/2001 | |

(Continued)

OTHER PUBLICATIONS

Dong, Jian; Liu, Zonglin; Han, Nianfeng; Wang, Qin; Xia, Yiran. "Preparation, morphology, and mechanical properties of elastomers based on α,ω—dihydroxy-polydimethylsiloxane/polystyrene blends", School of Chemistry and Chemical Engineering, Shandong University, Jinan, Peop. Rep. China. Journal of Applied Polymer Science (2004), 92(6), 3542-3548. Publisher: John Wiley & Sons, Inc., CODEN: JAPNAB ISSN: 0021-8995. Journal written in English. CAN 141:107480 AN 2004:416044 CAPLUS (Copyright® 2008 ACS on SciFinder® ).

Todd, et al. "Volatile Silicone Fluids for Cosmetics," Cosmetics and Toiletries, 91:29-32 (1976).

Balsam and Sagarin, Cosmetics, Science, and Technology, "Emollient Creams and Lotions," vol. 1, 27-104, 1972.

(Continued)

*Primary Examiner* — Bethany Barham
*Assistant Examiner* — Peter Anthopolos
(74) *Attorney, Agent, or Firm* — Schwegman Lundberg & Woessner, P.A.

(57) ABSTRACT

In various embodiments, provided are substantially homogenous swollen silicone gels, powders, pastes, and compositions thereof; methods of preparing the same; and personal care and healthcare products comprising the same.

14 Claims, 1 Drawing Sheet

(56) References Cited

FOREIGN PATENT DOCUMENTS

| | | | |
|---|---|---|---|
| JP | 2006-307004 | 11/2006 | ............ C08G 69/48 |
| JP | 2008-518082 | 5/2008 | ............... C08F 2/44 |
| JP | 2008-527077 | 7/2008 | ............. C08F 30/08 |
| JP | 2008-530338 | 8/2008 | ................ C08F 2/44 |
| JP | 2008-274249 A | 11/2008 | |
| JP | 2008-542462 | 11/2008 | ............ C08F 299/08 |
| JP | 2010-500437 A | 1/2010 | |
| JP | 2013-508510 A | 3/2013 | |
| WO | WO9840425 | 9/1998 | |
| WO | WO01/14458 | 3/2001 | |
| WO | WO02/28358 | 4/2002 | |
| WO | WO03/101412 | 12/2003 | |
| WO | WO03/105789 | 12/2003 | |
| WO | WO03/105801 | 12/2003 | |
| WO | WO03/106614 | 12/2003 | |
| WO | WO2004/000247 | 12/2003 | |
| WO | WO2004/054523 | 7/2004 | |
| WO | WO2004/054524 | 7/2004 | |
| WO | WO2004/060101 | 7/2004 | |
| WO | WO2004/060271 | 7/2004 | |
| WO | WO2004/060276 | 7/2004 | |
| WO | WO2006/088571 | 8/2006 | |
| WO | WO2007/007403 | 1/2007 | |
| WO | WO2007/007521 | 1/2007 | |
| WO | WO2007/109282 | 9/2007 | |
| WO | WO 2007139596 A2 * | 12/2007 | ............ B01J 31/146 |
| WO | WO2008/046762 | 4/2008 | |
| WO | WO-2007/109282 A3 | 5/2008 | |
| WO | WO2009/042732 | 4/2009 | |
| WO | WO-2011/049896 A2 | 4/2011 | |

OTHER PUBLICATIONS

Written Opinion of the International Searching Authority Application No. PCT/US2010/053112, dated Jun. 22, 2011, 6 pages.

International Search Report Application No. PCT/US2010/053112, dated Jun. 22, 2011, 3 pages.

Liles, Donald T.; Morita, Yoshitsugu; Kobayashi, Kazuo, Dow Corning Corporation, Midland, MI, USA. "Silicone Elastomeric Powders", *Polymer News*, 2002, vol. 27, pp. 406-411.

Ginam Kim, Alioscka Sousa, Deborah Meyers, Marilyn Shope, and Matthew Libera, "Diffuse Polymer Interfaces in Lobed Nanoemulsions Preserved in Aqueous Media" Dow Corning Corporation, Science and Technology, Midland, Michigan 48640, and Department of Chemical, Biomedical, and Materials Engineering, Stevens Institute of Technology, Hoboken, New Jersey 07030, 6570 J.AM. CHEM. SOC. 2006, 128, pp. 6570-6571.

Abstract to Darvishi, M. Rezaee; Mirzadeh, H.; Mehrabzadeh, M. Polymer Engineering Department, Amir Kabir University of Technology, Tehran, Iran, "Preparation and study of physical and mechanical properties of biocompatible blends based on poly(dimethylsiloxane) (PDMS) and poly(2-hydroxyethyl methacrylate) (PHEMA)", Iranian Journal of Polymer Science and Technology (Persian Edition) (1998), 11(3), 155-162. Publisher: Iran Polymer Institute, CODEN: IJPTEH ISSN: 1017-6020. Journal written in Persian. CAN 131:59820 AN 1999:269094 CAPLUS.

Newton, Joanna, Stoller, Catherine, and Starch, Michael, "Silicone Technology Offers Novel Methods for Delivering Active Ingredients", Dow Corning Corporation, Midland, Michigan, 5 pages.

Written Opinion of the International Searching Authority Application No. PCT/US2010/053145, dated Dec. 21, 2010, 5 pages.

International Search Report Application No. PCT/US2010/053145, dated Dec. 21, 2010, 3 pages.

"Chinese Application Serial No. 201080053557.1, Office Action mailed Apr. 10, 2014", 5 pgs.

"Chinese Application Serial No. 201080053557.1, Office Action mailed Aug. 6, 2013", 7 pgs.

"Chinese Application Serial No. 201080053557.1, Office Action mailed Nov. 3, 2014", 7 pgs.

"Chinese Application Serial No. 201080053557.1, Response filed Jun. 25, 2014 to Office Action mailed Apr. 10, 2014", 26 pgs.

"Chinese Application Serial No. 201080053557.1, Response filed Dec. 12, 2013 to Office Action mailed Aug. 6, 2013", 11 pgs.

"Chinese Application Serial No. 201080053557.1, Voluntary Amendment filed Jan. 25, 2013", 25 pgs.

"European Application Serial No. 10821448.7, Communication pursuant to Rules 161 and 162 EPC mailed May 31, 2012", 2 pgs.

"European Application Serial No. 10821448.7, Response filed Nov. 16, 2012 to Communication pursuant to Rules 161 and 162 EPC mailed May 31, 2012", 20 pgs.

"International Application Serial No. PCT/US2010/053112, International Preliminary Report on Patentability mailed May 3, 2012", 8 pgs.

"Japanese Application Serial No. 2012-535287, Office Action mailed Sep. 9, 2014", 10 pgs.

"Japanese Application Serial No. 2012-535287, Response filed Dec. 9, 2014 to Office Action mailed Sep. 9, 2014", 2 pgs.

"Korean Application Serial No. 10-2012-7012268, Amendment filed May 24, 2012", 11 pgs.

* cited by examiner

SILICONE COMPOSITIONS COMPRISING A SWOLLEN SILICONE GEL

CROSS-REFERENCE TO RELATED APPLICATIONS

This application is a U.S. National Stage of International Application No. PCT/US2010/053112, filed Oct. 19, 2010, which claims the benefit of U.S. Provisional Application No. 61/254,476, filed Oct. 23, 2009, each of which is hereby incorporated by reference herein in its entirety.

A swollen silicone gel composition can be generally characterized as having a cross-linked polymer matrix (elastomer) component and a fluid component that is sufficiently compatible with the elastomer such that the fluid swells the elastomer. Compositions comprising such gels have been found to be particularly useful in personal care applications because of their ability to introduce a fluid to skin or hair while imparting a smooth, silky, low-residue feel on drydown. The fluid component can also be used as a carrier for other compounds, such as active ingredients, thereby allowing them to become be trapped within the matrix of the silicone gel. Thus, compositions comprising silicone gels are useful for delivery of a wide variety of active ingredients such as pharmaceutical agents, vitamins, fragrances, oils, and lotions for delivery in cosmetics and personal care products.

US 2008/0085983 A1 describes methods of making silicone microparticles by organoborane-amine complex-catalyzed free radical polymerization or cross-linking of organic or organosilicon monomers, oligomers, and/or polymers in the presence of a poor solvent (a fluid in which the polymerization product is not substantially soluble at the reaction temperature) or a non-solvent (a fluid in which the polymerization product is essentially insoluble at the reaction temperature) for the resulting polymer. Thus, the described methods involve heterogeneous polymerization of microparticles, as the polymer particles have low or no solubility in the solvent and the solvent is not carried by the silicone microparticles because of limited uptake. Since the solvent is not absorbed, it does not cause silicone elastomer to swell, nor does it act as a carrier for other components such as active ingredients.

Thus, there remains a need for facile, cost-effective methods of preparing silicone compositions that can be used for the delivering compounds such as active ingredients.

This need is met by silicone compositions and methods of making such compositions provided by the present invention. According to some embodiments, the compositions comprise a substantially homogenous swollen silicone gel. Such gels comprise an elastomeric matrix formed by polymerization of organopolysiloxanes in the presence of an organoborane compound and a miscible fluid, wherein the elastomer formed absorbs the miscible fluid. Compositions comprising such gels are useful in a variety of applications, including but not limited to, delivery of active ingredients for personal care and healthcare products. In some aspects, the compositions comprise thermally-sensitive active ingredients.

According to some aspects, silicone compositions are prepared by a method comprising polymerizing Component (A), at least one free radical polymerizable organopolysiloxane; wherein polymerization occurs in the presence of Component (B), at least one organoborane free radical initiator; Component (C), at least one miscible fluid; and oxygen to form a substantially homogenous swollen elastomeric gel. In some embodiments, the elastomer formed is compatible with and absorbs Component (C). Such gels are characterized, in part, as having a plateau elastic shear modulus that is less than or equal to half the intrinsic plateau elastic shear modulus of the elastomer in its undiluted state. In some aspects, the silicone gel compositions may be formed into powders, pastes, and/or used in personal care and healthcare products.

These and additional features and advantages of the invention will become apparent in the course of the following detailed description.

A more complete appreciation of the invention and the many embodiments thereof will be readily obtained as the same becomes better understood by reference to the following detailed description when considered in connection with the accompanying drawings, wherein.

Features and advantages of the invention will now be described with occasional reference to specific embodiments. However, the invention may be embodied in different forms and should not be construed as limited to the embodiments set forth herein. Rather, these embodiments are provided so that this disclosure will be thorough and complete and will fully convey the scope of the invention to those skilled in the art.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

The term "independently selected from," as used in the specification and appended claims, is intended to mean that the referenced groups can be the same, different, or a mixture thereof, unless the context clearly indicates otherwise. Thus, under this definition, the phrase "$X^1$, $X^2$, and $X^3$ are independently selected from noble gases" would include the scenario where $X^1$, $X^2$, and $X^3$ are all the same, where $X^1$, $X^2$, and $X^3$ are all different, and where $X^1$ and $X^2$ are the same but $X^3$ is different.

As used in the specification and appended claims, the term "miscible fluid" is intended to mean a polar or non-polar fluid capable of acting as a solvent for Component (A) and that is also sufficiently compatible with the resulting elastomer to be absorbed as a diluent. Examples of fluids suitable for polymer systems can be found in standard polymer handbooks, such as the Polymer Handbook, Third Edition, Edited by J. Brandrup and E. H. Immergut, John Wiley & Sons, Pages VII/379-382+, (1989).

"Plateau elastic shear modulus," as the term is used in the specification and appended claims, is defined experimentally by the median value of dynamic elastic shear modulus (G') in the region of the plot of G' vs. testing frequency where G' reaches a relatively constant value (or exhibits a "plateau") as determined, for example, by a small strain dynamic oscillatory shear experiment. One skilled in the art would know that appropriate strain values are dictated by the sensitivity of the particular rheometer, sampling geometry, and material chosen and can be any value of strain that falls within the small strain regime where G' is independent of strain, as determined for example by a strain sweep experiment. G' is a material function that is independent of method.

The term "viscosity," as used in the specification and appended claims that pertain to pastes, is intended to mean the value of the real component of the complex viscosity ($\eta'$) measured with a rheometer. Examples of suitable rheometers include, but are not limited to, a Rheometrics RDA II parallel plate rheometer, using a small strain dynamic oscillatory shear experiment at an angular frequency of 10 rad/s; and a Brookfield DV-II+ rheometer with a Helipath attachment and T-D spindle (20.4 mm crossbar) at 2.5 rpm, following the manufacturer's recommended testing procedure and measuring at 25° C. η' is a material function that is independent of method. For simple polymers and fluids, such as the individual components comprising the elastomeric compositions, "viscosity" refers to an extrapolated zero shear viscosity as measured in a small strain dynamic oscillatory shearing experiment at shear rates low enough for η' to be relatively independent of shear rate. For pastes, "viscosity" in the examples of this application refer to the measured value of η' at the stated frequency and strain rate.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The present invention relates generally to elastomeric silicone gels, powders, pastes, and compositions thereof; methods of preparing the same; and personal care and healthcare products comprising the same. In various embodiments, provided are silicone compositions comprising Component (A), at least one free radical polymerizable organopolysiloxane; Component (B), at least one organoborane free radical initiator; Component (C), at least one miscible fluid; optional Component (D), at least one organonitrogen-reactive compound; optional Component (E), at least one free radical polymerizable organic co-monomer; and optional Component (F), at least one active ingredient suitable for use in personal care and healthcare products; or the reaction product(s) of two or more components.

In various embodiments, also provided are methods for the preparation of silicone compositions. Such methods comprise polymerizing Component (A); wherein polymerization occurs in the presence of Component (B), Component (C), optionally Component (D), optionally Component (E), and optionally Component (F) in the presence of oxygen while maintaining the temperature at from about 5° C. to about 95° C. (alternatively, from about 10° C. to about 35° C.) to form a substantially homogenous swollen silicone elastomeric gel. In some embodiments, the elastomer of such gel is compatible with and absorbs Component (C). In some embodiments, the gel formed has a plateau elastic shear modulus not greater than one half of the intrinsic plateau elastic shear modulus of the silicone elastomer in its undiluted state.

Component (A), Free Radical Polymerizable Organopolysiloxane

Generally, Component (A) comprises organopolysiloxanes having free radical polymerizable groups. Said organopolysiloxanes can be polymeric or a mixture of oligomers and polymers, and polymeric organopolysiloxanes can either be homopolymeric or heteropolymeric. In addition, the organopolysiloxanes can be linear, branched, hyperbranched or resinous in structure. Component (A) undergoes free radical-catalyzed addition polymerization, and in some aspects, can also undergo co-polymerization and/or cross-linking.

In some aspects, Component (A) comprises organopolysiloxanes having at least two free radical polymerizable moieties per molecule, wherein such moieties are monofunctional, multifunctional, or a combination thereof. Thus, Component (A) can be a mixture of organopolysiloxanes differing in their degree of functionality and/or the nature of the free radical polymerizable moieties. The organopolysiloxanes of Component (A) can also vary in consistency from a fluid to a gum. For example, the organopolysiloxane can be a fluid, a solid, or a solid that becomes flowable at an elevated temperature or by the application of shear. In some aspects, the organopolysiloxanes have a viscosity of from about 1 cP to about 5,000,000 cP at 25° C.; alternatively, from about 50 cP to about 500,000 cP at 25° C.; alternatively, from about 100 cP to about 100,000 cP at 25° C.

The organopolysiloxanes of Component (A) may also have a glass transition temperature or, upon polymerization or crosslinking, form particles that have a glass transition temperature, wherein the resulting silicone composition undergoes marked changes in its viscosity under the temperatures of use. Such compositions are particularly useful for encapsulation of active ingredients that are released by the introduction of heat.

In some aspects, Component (A) may comprise free radical polymerizable organopolysiloxanes having formulae selected from:

$$R^1_3SiO(R^1_2SiO)_a(R^1R^2SiO)_bSiR^1_3;\quad (1)$$

wherein a has a value of zero to 20,000 and b has a value of 1 to 20,000; and wherein each $R^1$ group is independently a hydrogen, halogen, or a monovalent organic group, and each $R^2$ group is independently a monovalent unsaturated organic group; and $$R^3_2R^4SiO(R^3_2SiO)_c(R^3R^4SiO)_dSiR^3_2R^4;\quad (2)$$

wherein c has a value of zero to 20,000, and d has a value of zero to 20,000; and wherein each $R^3$ is independently a hydrogen, halogen, or a monovalent organic group, and each $R^4$ group is independently a monovalent unsaturated organic group.

Suitable $R^1$ and $R^3$ groups include, but are not limited to, hydrogen; organic groups (linear and/or branched) such as alkyl groups, haloalkyl groups, alkenyl groups, alkynyl groups, acrylate functional groups, and methacrylate functional groups; and other organic functional groups such as glycidyl groups, amine groups, ether groups, cyanate ester groups, isocyano groups, ester groups, carboxylic acid groups, carboxylate salt groups, succinate groups, anhydride groups, mercapto groups, sulfide groups, azide groups, phosphonate groups, phosphine groups, masked isocyano groups, and hydroxyl groups. Examples of such groups include, but are not limited to, acrylate functional groups such as acryloyloxypropyl groups and methacryloyloxypropyl groups; alkyl groups such as methyl, ethyl, propyl, isopropyl, n-butyl, s-butyl, and t-butyl groups; alkenyl groups such as vinyl, allyl, and butenyl groups; alkynyl groups such as ethynyl and propynyl groups; aromatic groups such as phenyl, tolyl, and xylyl groups; cyanoalkyl groups such as cyanoethyl and cyanopropyl groups; halogenated hydrocarbon groups such as 3,3,3-trifluoropropyl, 3-chloropropyl, dichlorophenyl, and 6,6,6,5,5,4,4,3,3-nonafluorohexyl groups; alkenyloxypoly(oxyalkyene) groups such as allyloxy(polyoxyethylene), allyloxypoly(oxypropylene), and allyloxy-poly(oxypropylene)-co-poly(oxyethylene) groups; alkyloxypoly(oxyalkyene) groups such as propyloxy(polyoxyethylene), propyloxypoly(oxypropylene), and propyloxy-poly(oxypropylene)-co-poly(oxyethylene) groups; halogen substituted alkyloxypoly (oxyalkyene) groups such as perfluoropropyloxy (polyoxyethylene), perfluoropropyloxypoly(oxypropylene), and perfluoropropyloxy-poly(oxypropylene)-co-poly(oxyethylene) groups; alkoxy groups such as methoxy, ethoxy, n-propoxy, isopropoxy, n-butoxy, and ethylhexyloxy groups; aminoalkyl groups such as 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole groups; epoxyalkyl groups such as 3-glycidoxypropyl, 2-(3,4,-epoxycyclohexyl)ethyl, and 5,6-epoxyhexyl groups; ester functional groups such as actetoxyethyl and benzoyloxypropyl groups; hydroxy functional groups such as hydroxy and 2-hydroxyethyl groups; isocyanate and masked isocyanate functional groups such as 3-isocyanatopropyl, tris-3-propyl-isocyanurate, propyl-t-butylcarbamate, and propylethylcarbamate groups; aldehyde functional groups such as undecanal and butyraldehyde groups; anhydride functional groups such as 3-propyl succinic anhydride and 3-propyl maleic anhydride groups; carboxylic acid functional groups such as 3-carboxypropyl and 2-carboxyethyl groups; and metal salts of carboxylic acids such as the zinc, sodium, or potassium salts of 3-carboxypropyl and 2-carboxyethyl.

Suitable $R^2$ and $R^4$ groups include, but are not limited to, monovalent alkenyl and alkynyl groups having 2-12 carbon atoms groups such as vinyl, allyl, butenyl, ethynyl, and propynyl groups; alkenyloxypoly(oxyalkyene) groups such as allyloxy(polyoxyethylene), allyloxypoly(oxypropylene), and allyloxy-poly(oxypropylene)-co-poly(oxyethylene) groups; acrylate functional groups such as acryloyloxypropyl and methacryloyloxypropyl groups; and halogen-substituted analogs thereof. In certain aspects, $R^2$ and $R^4$ are selected from acrylate groups and methacrylate groups.

Some representative examples of Component (A) include, but are not limited to, methacryloxypropyldimethylsiloxy-terminated polydimethylsiloxane; acryloxypropyldimethylsiloxy-terminated polydimethylsiloxane, 1,3-bis(methacryloxypropyl)tetramethyldisiloxane, 1,3-bis(acryloxypropyl) tetramethyldisiloxane, 1,3-bis(methacryloxymethyl) tetramethyldisiloxane, 1,3-bis(acryloxymethyl) tetramethyldisiloxane, α,ω,-methacryloxymethyldimethylsilyl terminated polydimethylsiloxane, methacryloxypropyl-terminated polydimethylsiloxane, α,ω-acryloxymethyldimethylsilyl terminated polydimethylsiloxane, methacryloxypropyldimethylsilyl terminated polydimethylsiloxane, α,ω-acryloxypropyldimethylsilyl terminated polydimethylsiloxane, pendant acrylate and methacrylate functional polymers such as poly(acryloxypropyl-methylsiloxy) polydimethylsiloxane and poly(methacryloxypropyl-methylsiloxy) polydimethylsiloxane copolymers, telechelic polydimethylsiloxanes having multiple acrylate or methacrylate functional groups including those formed via a Michael addition reaction of multi-acrylate or multi-methacrylate monomers to amine-terminated polydimethylsiloxanes, and combinations thereof. Also suitable for use as free radical polymerizable organosilicon compounds include monofunctional acrylate or methacrylate terminated organopolysiloxanes such as polydimethylsiloxane terminated at one end by a methacryloxypropyldimethylsilyl group and terminated at the other end by n-butyldimethylsilyl groups.

In some aspects, Component (A) may comprise siloxane resins having structural units of organopolysiloxanes independently selected from:

wherein M represents a monofunctional unit $R_3SiO_{1/2}$; D represents a difunctional unit $R_2SiO_{2/2}$; T represents a trifunctional unit $RSiO_{3/2}$; and Q represents a tetrafunctional unit $SiO_{4/2}$, where "R" represents any suitable functional group.

In some aspects, Component (A) may comprise a siloxane resin selected from MQ resins having $R^5_3SiO_{1/2}$ units and $SiO_{4/2}$ units; TD resins having $R^5SiO_{3/2}$ units and $R^5_2SiO_{2/2}$ units; MT resins having $R^5_3SiO_{1/2}$ units and $R^5SiO_{3/2}$ units; MTD resins having $R^5_3SiO_{1/2}$ units, $R^5SiO_{3/2}$ units, and $R^5_2SiO_{2/2}$ units, and combinations thereof; wherein each $R^5$ group is independently a monovalent organic group having from 1-20 carbon atoms. In some aspects, $R^5$ has from 1-10 carbon atoms. In some aspects, at least one $R^5$ group is a free radical polymerizable unsaturated organic group.

Suitable examples of $R^5$ include, but are not limited to, acrylate functional groups such as acryloxyalkyl groups; methacrylate functional groups such as methacryloxyalkyl groups; cyano functional groups; monovalent hydrocarbon groups; and combinations thereof. The monovalent hydrocarbon groups may include alkyl groups such as methyl, ethyl, propyl, isopropyl, n-butyl, s-butyl, t-butyl, pentyl, neopentyl, octyl, undecyl, and octadecyl groups; cycloalkyl groups such as cyclohexyl groups; alkenyl groups such as vinyl, allyl, butenyl, and hexenyl groups; alkynyl groups such as ethynyl, propynyl, and butynyl groups; aryl groups such as phenyl, tolyl, xylyl, benzyl, and 2-phenylethyl groups; halogenated hydrocarbon groups such as 3,3,3-trifluoropropyl, 3-chloropropyl, dichlorophenyl, and 6,6,6,5,5,4,4,3,3-nonafluorohexyl groups; and combinations thereof. The cyano-functional groups may include cyanoalkyl groups such as cyanoethyl and cyanopropyl groups, and combinations thereof.

$R^5$ may also include alkyloxypoly(oxyalkyene) groups such as propyloxy(polyoxyethylene), propyloxypoly(oxypropylene) and propyloxy-poly(oxypropylene)-co-poly (oxyethylene) groups, halogen substituted alkyloxypoly (oxyalkyene) groups such as perfluoropropyloxy (polyoxyethylene), perfluoropropyloxypoly(oxypropylene) and perfluoropropyloxy-poly(oxypropylene) copoly(oxyethylene) groups, alkenyloxypoly(oxyalkyene) groups such as allyloxypoly(oxyethylene), allyloxypoly(oxypropylene) and allyloxy-poly(oxypropylene) copoly(oxyethylene) groups, alkoxy groups such as methoxy, ethoxy, n-propoxy, isopropoxy, n-butoxy and ethylhexyloxy groups, aminoalkyl groups such as 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole groups, hindered aminoalkyl groups such as tetramethylpiperidinyl oxypropyl groups, epoxyalkyl groups such as 3-glycidoxypropyl, 2-(3,4,-epoxycyclohexyl)ethyl, and 5,6-epoxyhexyl groups, ester functional groups such as acetoxymethyl and benzoyloxypropyl groups, hydroxyl functional groups such as hydroxy and 2-hydroxyethyl groups, isocyanate and masked isocyanate functional groups such as 3-isocyanatopropyl, tris-3-propyl-isocyanurate, propyl-t-butylcarbamate, and propylethylcarbamate groups, aldehyde functional groups such as undecanal and butyraldehyde groups, anhydride functional groups such as 3-propyl succinic anhydride and 3-propyl maleic anhydride groups, carboxylic acid functional groups such as 3-carboxypropyl, 2-carboxyethyl, and 10-carboxydecyl groups, metal salts of carboxylic acids such as zinc, sodium, and potassium salts of 3-carboxypropyl and 2-carboxyethyl groups, and combinations thereof.

Some specific examples of suitable siloxane resins that can be used as Component (A) include, but are not limited to, $M^{Methacryloxymethyl}Q$ resins; $M^{Methacryloxypropyl}Q$ resins; $MT^{Methacryloxymethyl}T$ resins; $MT^{Methacryloxypropyl}T$ resins; $MDT^{Methacryloxymethyl}T^{Phenyl}T$ resins; $MDT^{Methacryloxypropyl}T^{Phenyl}T$ resins; $M^{Vinyl}T^{Phenyl}$ resins; $TT^{Methacryloxymethyl}$ resins; $TT^{Methacryloxypropyl}$ resins; $T^{Phenyl}T^{Methacryoxymethyl}$ resins; $T^{Phenyl}T^{Methacryloxypropyl}$ resins; $TT^{Phenyl}T^{Methacryloxymethyl}$ resins; $TT^{Phenyl}T^{Methacryloxypropyl}$ resins; and combinations thereof.

Siloxane resins may be prepared by any method known in the art. In some aspects, the resin is made by treating a resin copolymer produced by a silica hydrosol capping process with an alkenyl including endblocking reagent. This preferably includes reacting a silica hydrosol under acidic conditions with a hydrolyzable triorganosilane such as trimethylchlorosilane, a siloxane such as hexamethyldisiloxane, and combinations thereof, and then recovering a copolymer having M and Q groups including 2 to 5% wt of hydroxyl groups. The copolymer may be reacted with an endblocking agent including unsaturated organic groups and an endblocking agent free of aliphatic unsaturation in amounts sufficient to provide 3 to 30 mole percent of unsaturated organofunctional M, D or T groups in the resin relative to the sum of all M, D, T and Q units comprising the resin. Suitable endblocking agents include silazanes, siloxanes, silanes, and combinations thereof.

In some aspects, Component (A) is selected from acrylate and methacrylate-functional polydimethylsiloxanes and resins, methacryloxypropyldimethylsiloxy-terminated polydimethylsiloxane, methacryloxymethylsiloxy-terminated polydimethylsiloxanes, acryloxypropyldimethylsiloxy-terminated polydimethylsiloxanes, acryloxymethyldimethylsiloxy-terminated polydimethylsiloxanes, polydimethylsiloxane-polymethyl-methacryloxypropylsiloxane copolymers and polydimethylsiloxane-polymethyl-acryloxypropylsiloxane copolymers.

Component (B), Organoborane Free Radical Initiator

Generally, Component (B) comprises at least one organoborane compound that is capable of generating a free radical and initiating free radical addition polymerization and/or crosslinking. Stabilized organoborane compounds that render the organoborane non-pyrophoric at ambient conditions may be used. In some aspects, Component (B) is a complex formed between an organoborane and a suitable organonitrogen (for example, an amine) that renders the complex stable at ambient conditions, wherein a free radical is generated (and polymerization is initialized) upon introduction of an organonitrogen-reactive compound in the presence of oxygen. In some aspects, Component (B) is an organoborane compound wherein a free radical is generated (and polymerization is initiated) upon heating. In some aspects, Component (B) is a solvent-stabilized organoborane (for example, a solution of a trialkylborane in THF) where the solvent is allowed to evaporate to liberate the borane and thereby create a radical.

In some aspects, Component (B) is an organoborane-organonitrogen complex that may be selected from complexes having the formula:

wherein B represents boron and N represents nitrogen; wherein at least one of R6, R7, and R8 contains one or more silicon atoms with the silicon-containing group(s) covalently attached to boron; wherein R6, R7, and R8 are groups that can be independently selected from hydrogen, a cycloalkyl group, a linear or branched alkyl group having 1-12 carbon atoms on the backbone, an alkylaryl group, an organosilane group such as an alkylsilane or an arylsilane group, an organosiloxane group, an alkylene group capable of functioning as a covalent bridge to another boron atom, a divalent organosiloxane group capable of function as a covalent bridge to another boron atom, or halogen substituted homologues thereof; wherein R9, R10, and R11 are groups that yield an amine compound or a polyamine compound capable of complexing with boron and are independently selected from hydrogen, an alkyl group containing 1-10 carbon atoms, a halogen substituted alkyl group containing 1-10 carbon atoms, or an organosilicon functional group; and wherein at least two of the R6, R7, and R8 groups and at least two of the R9, R10, and R11 groups can combine to form heterocyclic structures, provided that the sum of the number of atoms from the two combining groups does not exceed 11.

In some aspects, Component (B) may be selected from alkylborane-organonitrogen complexes that include, but are not limited to, trialkylborane-organonitrogen complexes comprising trialkylboranes having the formula $BR''_3$, wherein R" represents linear and branched aliphatic or aromatic hydrocarbon groups containing 1-20 carbon atoms. Examples of suitable trialkylboranes include, but are not limited to, trimethylborane, tri-n-butylborane, tri-n-octylborane, tri-sec-butylborane, tridodecylborane, and phenyldiethylborane.

Examples of suitable organonitrogens for forming the organoborane-organonitrogen complexes of Component (B) include, but are not limited to, 1,3 propane diamine; 1,6-hexanediamine; methoxypropylamine; pyridine; isophorone diamine; and silicon-containing amines such as 3-aminopropyltrimethoxysilane, 3-aminopropyltriethoxysilane, 2-(trimethoxysilylethyl)pyridine, aminopropylsilanetriol, 3-(m- aminophenoxy)propyltrimethoxysilane, 3-aminopropyldiisopropylmethoxysilane, aminophenyltrimethoxysilane, 3-aminopropyltris(methoxyethoxethoxy)silane, N-(2-aminoethyl)-3-aminopropyltrimethoxysilane, N-(6-aminohexyl)aminomethyltrimethoxysilane, N-(2-aminoethyl)-11-aminoundecyltrimethoxysilane, (aminoethylaminomethyl)pbenethyltrimethoxysilane, N-(2-aminoethyl)-3-aminopropylmethyldimethoxysilane, N-(2-aminoethyl)-3-aminoisobutylmethyldimethoxysilane, and (3-trimethoxysilylpropyl)diethylenetriamine.

In some aspects, nitrogen-containing compounds that may be useful for forming the organoborane-organonitrogen complexes of Component (B) may be selected from organopolysiloxanes having at least one amine functional group. Examples of suitable amine functional groups include, but are not limited to, 3-aminopropyl, 6-aminohexyl, 11-aminoundecyl, 3-(N-allylamino)propyl, N-(2-aminoethyl)-3-aminopropyl, N-(2-aminoethyl)-3-aminoisobutyl, p-aminophenyl, 2-ethylpyridine, and 3-propylpyrrole. Such organopolysiloxanes include, but are not limited to, those having formulas similar to the previously described formulas (1) and (2). Other nitrogen-containing compounds that may be useful for forming the organoborane-organonitrogen complexes of Component (B) include, but are not limited to, N-(3-triethyoxysilylpropyl)-4,5-dihydroimidazole, ureidopropyltriethoxysilane, siloxanes having formulas similar to the previously described formulas (1) and (2), and organopolysiloxane resins in which at least one group is an imidazole, amidine, or ureido functional group.

In some aspects, a free radical is generated by, and polymerization and/or crosslinking is initiated by, heating an organoborane compound (preferably organoborane-organonitrogen complex) or by simply exposing an anaerobically contained alkylborane of Component (B) to air. In some aspects, a free radical is generated by, and polymerization and/or crosslinking is initiated by, heating an organoborane-organonitrogen complex of Component (B), wherein heating causes dissociation of the complex. In some aspects, a free radical is generated by, and polymerization and/or crosslinking is initiated by, combining an organonitrogen-reactive compound of Component (D) with an organoborane-organonitrogen complex of Component (B) in an oxygen environment, wherein the combination causes dissociation of the complex. With respect to the latter, a free radical can be generated at temperatures below the dissociation temperature of the organoborane-organonitrogen complex, such as at or below ambient temperature.

Although organonitrogen-stabilized organoborane compounds are particularly useful as Component (B), one of skill in the art will understand that any organoborane may be used. Examples of alternate stabilized forms of organoboranes useful for this invention, include ring stabilized compounds, such as 9-BBN, or solvent complexed organoboranes such as trialkylborane-THF solutions.

In some aspects, Component (B) is a trialkylborane-organonitrogen complex wherein the trialkylborane is selected from triethylborane, tri-n-butylborane, tri-n-octylborane, tri-sec-butylborane, and tridodecylborane. In some aspects, Component (B) may be selected from triethylborane-propanediamine (TEB-PDA), triethylborane-butylimidazole (TEB-BI), and triethylborane-methoxypropylamine (TEB-MOPA) complexes, and tri-n-butyl methoxypropyl amine.

Component (C), Miscible Fluid

Generally, Component (C) comprises at least one miscible fluid that is sufficiently compatible with the silicone elastomer to cause swelling of the elastomer, in contrast to an immiscible fluid, such as a poor solvent or non-solvent. In some aspects, suitable miscible fluids may be selected from silicones; organic compounds; and "ecologically-friendly" solvents, such as ionic liquids and supercritical fluids; and mixtures thereof.

Examples of suitable silicones for Component (C) include, but are not limited to, low molecular weight linear or cyclic volatile silicones; non-volatile alkyl or aryl silicones; and low molecular weight linear or cyclic functional silicones. The silicone miscible fluid may be a single silicone or a mixture of silicones. In some aspects, Component (C) is a low molecular weight volatile methyl silicone (VMS) having an average unit formula of $(CH3)_xSiO_{(4-x)/2}$ in which x has an average value of from 2 to 3. Representative units in such VMS compounds are $(CH_3)_3SiO_{1/2}$ units and $(CH_3)_2SiO_{2/2}$ units, and there additionally may be $CH_3SiO_{3/2}$ units and/or $SiO_{4/2}$ units that result in the formation of branched, linear or cyclic volatile methyl silicones. Linear VMS have the formula $(CH_3)_3SiO\{(CH_3)_2SiO\}_ySi(CH_3)_3$ where y is 0 to 5. Cyclic VMS have the formula $\{(CH_3)_2SiO\}_z$ where z is 3 to 6. Typically these volatile methyl silicones have boiling points less than about 250° C. and viscosities of from about 0.65 to 5.0 centistokes ($mm^2/s$).

In some aspects, suitable silicones include, but are not limited to, linear volatile methyl silicones, such as hexamethyldisiloxane, octamethyltrisiloxane, decamethyltetrasiloxane, dodecamethylpentasiloxane, tetradecamethylhexasiloxane, and hexadecamethylheptasiloxane; cyclic volatile methyl silicones, such as hexamethylcyclotrisiloxane, octamethylcyclotetrasiloxane, decamethylcyclopentasiloxane, and dodecamethylcyclohexasiloxane; and branched volatile methyl silicones, such as heptamethyl-3-{(trimethylsilyl)oxy}trisiloxane, hexamethyl-3,3,bis{(trimethylsilyl)oxy}trisiloxane, and pentamethyl {(trimethylsilyl)oxycyclotrisiloxane.

In some aspects, non-volatile alkyl or aryl silicones include, but are not limited to, linear poly alkyl or aryl silicones, such as compounds of the formula $R^4_3SiO(R^4_2SiO)_mSiR^4_3$; and cyclic poly alkyl or aryl silicones, such as compounds of the formula $(R^4_2SiO)_n$; wherein $R^4$ is an alkyl group of 1 to 6 carbon atoms, or an aryl group such as phenyl, m has a value of 0 to 80, preferably 0 to 20 and n has a value of 0 to 9, preferably 4 to 6. These silicones have viscosities generally in the range of about 1 to 100 centistokes ($mm^2/s$). Other representative low molecular weight non-volatile silicones have the general structure $R^5_3SiO(R^5R^6SiO)_pSiR^5_3$ where p has a value to provide polymers with a viscosity in the range of about 100 to 10,000 centistokes ($mm^2/sec$) and $R^5$ and $R^6$ are alkyl radicals of 1 to 30 carbon atoms, or an aryl group such as phenyl. Typically, the value of p is about 60 to 600. Non-volatile polysiloxanes may be exemplified by, but are not limited to, polydimethylsiloxane, polydiethylsiloxane, polymethylethylsiloxane, polymethylphenylsiloxane, and polydiphenylsiloxane.

In some aspects, low molecular weight functional silicones can be represented by acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silanol functional siloxanes.

In some aspects, Component (C) may be selected from organic compounds. Examples include, but are not limited to, aromatic hydrocarbons; aliphatic hydrocarbons; alcohols; aldehydes; ketones; amines; esters; ethers; glycols; glycol ethers; alkyl halides; or aromatic halides. The organic miscible fluids may be further exemplified as alcohols, such as methanol, ethanol, 1-propanol, cyclohexanol, benzyl alcohol, 2-octanol, ethylene glycol, propylene glycol, and glycerol; aliphatic hydrocarbons, such as pentane, cyclohexane, heptane, VM&P solvent, and mineral spirits; alkyl halides, such as chloroform, carbon tetrachloride, perchloroethylene, ethyl chloride, and chlorobenzene; amines, such as isopropylamine, cyclohexylamine, ethanolamine, and diethanolamine; aromatic hydrocarbons, such as benzene, toluene, ethylbenzene, and xylene; esters, such as ethyl acetate, isopropyl acetate, ethyl acetoacetate, amyl acetate, isobutyl isobutyrate, and benzyl acetate; ethers, such as ethyl ether, o-butyl ether, tetrahydrofuran, and 1,4-dioxane; glycol ethers, such as ethylene glycol monomethyl ether, ethylene glycol monomethyl ether acetate, diethylene glycol monobutyl ether, and propylene glycol monophenyl ether; ketones, such as acetone, methyl ethyl ketone, cyclohexanone, diacetone alcohol, methyl amyl ketone, and diisobutyl ketone; petroleum hydrocarbons, such as gasoline, naphtha, kerosene, gas oil, heavy oil, and crude oil; lubricating oils such as spindle oil and turbine oil; and organic oils.

When component (C) is an organic oil, it may be selected from any organic oils known in the art suitable for use in the preparation of personal, household, or healthcare formulations. Suitable organic oils include, but are not limited to, natural oils such as coconut oil, corn oil, soybean oil, olive oil, rape seed oil, cotton seed oil, sardine oil, herring oil, and whale oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate. The organic oil components can also be mixture of low viscosity and high viscosity oils. Suitable low viscosity oils have a viscosity of 5 to 100 mPas at 25° C., and are generally esters having the structure RCO—OR' wherein RCO represents the carboxylic acid radical and wherein OR' is an alcohol residue. Examples of suitable low viscosity oils include, but are not limited to, isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof.

Suitable high viscosity oils generally have a viscosity of 200-1,000,000 mPas at 25° C., alternatively a viscosity of 100,000-250,000 mPas. Examples of suitable high viscosity oils include, but are not limited to, castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof.

Other organic compounds suitable for Component (C) include, but are not limited to, mineral oils such as liquid paraffin or liquid petroleum; animal oils such as perhydrosqualene oil; vegetable oils such as sweet almond, calophyllum, palm, castor, avocado, jojoba, olive or cereal germ oil; esters of lanolic acid, oleic acid, lauric acid, stearic acid or myristic acid; alcohols such as oleyl alcohol, linoleyl or linolenyl alcohol, isostearyl alcohol or octyldodecanol; and acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The organic oil may also be a volatile organic solvent. Suitable as a volatile organic solvent component are various C8-C20 isoparaffins such as C12 isoparaffin made by The Permethyl Corporation having the tradename Permethyl® 99A, or a C12 isoparaffin (isododecane). Various C16 isoparaffins commercially available, such as isohexadecane are also suitable. Other suitable volatile solvents are various fluoro containing materials such as Ethyl Perfluoroisobutyl Ether (and) Ethyl Perfluorobutyl Ether (3M Cosmetic fluid CF-76) and Cosmetic Fluid CF-61: Methyl Perfluoroisobutyl Ether (and) Methyl Perfluorobutyl Ether (3M Cosmetic Fluid CF-61).

The organic compound may also be selected from acetonitrile, nitromethane, dimethylformamide, propylene oxide, trioctyl phosphate, butyrolactone, furfural, pine oil, turpentine, and m-creosol; volatile flavoring agents; and other useful flavoring agents including aldehydes and esters; volatile fragrances such as natural products and perfume oils. The organic miscible fluid can be a single compound or a mixture of compounds. Additionally, Component (C) can be a mixture of an organic miscible fluid and other miscible fluids, such as a siloxane.

In some aspects, Component (C) may be an ionic fluid. Examples of suitable ionic fluids include, but are not limited to, imidazolium derivatives, such as 1-ethyl-3-methylimidazolium tosylate, 1-ethyl-3-methylimidazolium tetrafluoroborate, 1-methyl-3-octylimidazolium chloride, 1-ethenyl-3-ethyl-imidazolium hexafluorophosphate, 1-butyl-3-methylimidazolium hexafluorophosphate; and pyridinium derivatives, such as 1-butyl-4-methylpyridinium chloride, 1-butyl-4-methylpyridinium hexafluorophosphate, and 1-butyl-4-methylpyridinium tetrafluoroborate.

In some aspects, Component (C) may be a supercritical fluid. Examples of suitable supercritical fluids include, but are not limited to, supercritical carbon dioxide, supercritical water, supercritical ethane, supercritical nitrous oxide, supercritical ammonia; supercritical 1,1,1,2-tetrafluoroethane; supercritical difluoromethane; supercritical pentafluoroethane; and mixtures thereof. The solvent strength of supercritical fluids may also be modified by any number of co-solvents such as methanol, ethanol, acetone, hexane, or benzene.

Examples of a suitable Component (C) for the polymerization of radical-polymerizable polydimethylsiloxanes include, but are not limited to, hexane, cyclohexane, heptane, hexamethyldisiloxane, octamethyltrisiloxane, octamethylcyclotetrasiloxane, decamethylcyclopentasiloxane, decamethyltetrasiloxane, isododecane, isohexadecane, isodecylneopentanoate, isononyl isononanoate, isoparaffin, isoalkane, and capryloylmethyl trisiloxane, toluene, ethyl acetate, 1-ethenyl-3-ethyl-imidazolium hexafluorophosphate, tetrapropyl-ammonium tetracyanoborate, and trimethylsilyl-terminated polydimethylsiloxane fluids having a viscosity of less than 1000 cP at 25° C., or a mixture thereof. In some aspects, the trimethylsilyl-terminated polydimethylsiloxane fluids chosen as Component (C) have a viscosity of from about 0.5 to about 100 cP at 25° C.

Optional Component (D), Organonitrogen-Reactive Compound

Generally, optional Component (D) comprises at least one organonitrogen-reactive compound that, when combined with the organoborane-organonitrogen complex of Component (B) and exposed to an oxygenated environment such as ambient air, is capable of causing the organoborane-organonitrogen complex to dissociate, thereby initiating free radical polymerization and/or crosslinking. The presence of such an organonitrogen-reactive compound allows for polymerization and/or crosslinking to occur rapidly at temperatures below the dissociation temperature of the organoborane-organonitrogen complexes of Component (B), including at room temperature and below.

Some examples of suitable organonitrogen-reactive compounds of Component (D) include, but are not limited to, mineral acids, Lewis acids, carboxylic acids, carboxylic acid derivatives such as anhydrides and succinates, carboxylic acid metal salts, isocyanates, aldehydes, epoxides, acid chlorides, and sulphonyl chlorides, acetic acid, acrylic acid, methacrylic acid, polyacrylic acid, polymethacrylic acid, methacrylic anhydride, undecylenic acid, oleic acid, citric acid, stearic acid, levulinic acid, 2-carboxyethyl acrylate, isophorone diisocyanate monomers or oligomers, methacryloylisocyanate, 2-(methacryloyloxy)ethyl acetoacetate, undecylenic aldehyde, and dodecyl succinic anhydride.

Additionally, organosilanes or organopolysiloxanes having organonitrogen-reactive groups can be suitable for Component (D). Such compounds include, but are not limited to, 3-isocyanatopropyltrimethoxysilane; 3-glycidoxypropyltrimethoxysilane; propylsuccinic anhydride functionalized linear, branched, resinous, and hyperbranched organopolysiloxanes; cyclohexenyl anhydride functional linear, resinous, and hyperbranched organopolysiloxanes; carboxylic acid functionalized linear, branched, resinous, and hyperbranched organopolysiloxanes such as carboxydecyl terminated oligomeric or polymeric polydimethylsiloxanes; and aldehyde functionalized linear, branched, resinous, and hyperbranched organopolysiloxanes such as undecylenic aldehyde-terminated oligomeric or polymeric polydimethylsiloxanes.

Other suitable organonitrogen-reactive compounds for Component (D) are silicon containing compounds that, when exposed to moisture, release an acid that causes the organoborane-organonitrogen complex of Component (B) to disassociate. Such compounds include, but are not limited to, halo silanes, acid anhydride (carboxylic acid) siloxanes, acetoxy siloxanes (such as ethylriacetoxysiloxane and methyl triacetoxysiloxane), alkyl silicic acids, esters of carboxylic acids and silanols, acid chloride siloxanes.

Further examples of compounds that can be useful for Component (D) are those capable of generating organonitrogen-reactive groups when exposed to ultraviolet radiation, such as iodonium salts containing $[SbF_6]^-$ counterions. With such compounds, it may be useful to also include a photosensitizing compound such as isopropylthioxanthone.

One of skill in the art will recognize that the selection of the organonitrogen-reactive compound for Component (D) will depend upon, among other things, the nature of Component (B). Good results have been obtained with the selection of isophorone diisocyanate, acetic acid, and carboxyl-terminated polydimethylsiloxanes as Component (D).

When an organonitrogen-reactive compound is used in the silicone composition, free radical generation requires the presence of oxygen. In some aspects, merely exposing the organonitrogen-reactive compound or the composition containing the organonitrogen-reactive compound to air is sufficient to induce polymerization. In some aspects, the oxygen dissolved in one or more of the other components of the composition, such as the miscible fluid, is sufficient. It is to be understood that limiting the concentration of oxygen, such as imposed by the use of a nitrogen sweep or purge, may be advantageous for safety (reduced flammability of volatile fluids) and/or for reaction efficiency as long as oxygen is not completely precluded from the system. To prevent premature polymerization in the presence of oxygen, Component (B) and Component (D) may be physically or chemically isolated until just prior to the desired time to initiate polymerization and/or crosslinking reactions. For example, the composition may be prepared initially as two separate solutions that are combined into one, just prior to the initiation of polymerization and/or crosslinking. The remaining components of the composition may be distributed in any manner between the two solutions, as long as Component (B) and Component (D) do not contact each other. For example, a first solution comprising Components (A) and (B), and a second solution comprising components (C) and (D) are air stable, but polymerize to form fine particles when the solutions are mixed together in presence of air. Alternatively, components (B) and (D), or both, can be encapsulated or delivered in separate phases. For example, one or both of the Components (B) and (D) can be introduced into the silicone composition in a solid form that prevents their intimate mixing. Polymerization of the composition can be activated by (a) heating it above the softening temperature of the solid phase component or encapsulant, or (b) by the introduction of a solubilizing agent that allows mixing of components (B) and (D). Alternatively, Components (B) and (D) can be combined and packaged anaerobically in a single container, and polymerization can be initiated by introduction of oxygen to the composition.

In some aspects, an optional organonitrogen-reactive compound is not a component of the silicone composition. In such cases, free radical polymerization may be initiated by exposing the organoborane compound to air, by thermal activation, or via radiation. In the case of thermal activation, the temperature to which the one or more components of the composition must be heated to initiate polymerization is dictated by the nature of the organoborane compound selected as Component (B). For example, if an organoborane-organonitrogen complex is selected as Component (B), the binding energy of the complex will dictate the temperature to which the composition must be heated to initiate dissociation of the complex and polymerization. In some aspects, Component (B) may be heated prior to its introduction with the other components of the composition. In other aspects, Component (B) and at least one other component are heated prior to the introduction of any remaining components of the composition.

Optional Component (E), Polymerizable Co-Monomer

Generally, optional Component (E) comprises at least one organic co-monomer capable of free radical polymerization. In some aspects, Component (E) is a free radical polymerizable organic co-monomer having at least one hydrophilic group. Examples of suitable organic compounds include, but are not limited to, 2-ethylhexylacrylate, 2-ethylhexylmethacrylate, methylacrylate, methylmethacrylate, neopentyl glycol diacrylate, neopentyl glycol dimethacrylate, glycidyl acrylate, glycidyl methacrylate, allyl acrylate, allyl methacrylate, stearyl acrylate, tetrahydrofuryl methacrylate, caprolactone acrylate, acrylic acid, methacrylic acid, 2-hydroxyethylacrylate, 2-hydroxyethylmethacrylate, perfluorobutyl acrylate, perfluorobutyl methacrylate, 1H, 1H, 2H, 2H-heptadecafluorodecyl acrylate, 1H, 1H, 2H, 2H-heptadecafluorodecyl methacrylate, tetrahydroperfluoro acrylate, phenoxyethyl acrylate, phenoxyethyl methacrylate, bisphenol A acrylate, bisphenol A dimethacrylate, ethoxylated bisphenol A acrylate, ethoxylated bisphenol A methacrylate, hexafluoro bisphenol A diacrylate, hexafluoro bisphenol A dimethacrylate, diethylene glycol diacrylate, diethylene glycol dimethacrylate, dipropylene glycol diacrylate, dipropylene glycol dimethacrylate, polyethylene glycol diacrylate, polyethylene glycol acrylate, polyethylene glycol methacrylate, polyethylene glycol dimethacrylate, polypropylene glycol acrylate, polypropylene glycol methacrylate, polypropylene glycol diacrylate, polypropylene glycol dimethacrylate, propylene glycol mono-methacrylate, ethylene glycol monomethacrylate, N-isopropyl acrylamide, trimethylolpropane triacrylate, trimethylolpropane trimethacrylate, ethoxylated trimethylolpropane triacrylate, ethoxylated trimethylolpropane trimethacrylate, pentaerythritol triacrylate, pentaerythritol trimethacrylate, pentaerythritol tetraacrylate, pentaerythritol tetramethacrylate, methyl-3-butenoate, allyl methyl carbonate, diallyl pyrocarbonate, allyl acetoacetate, diallyl carbonate, diallyl phthalate, dimethyl itaconate, diallyl carbonate, or combinations thereof. Other useful organic compounds include acrylate tipped polyurethane prepolymers prepared by reacting isocyanate reactive acrylate monomers, oligomers or polymers such as hydroxy acrylates with isocyanate functional prepolymers. One of skill in the art will recognize that the selection of the organic compound for Component (E) will depend upon, among other things, the nature of Component (A) and the desired use of the resulting product. Good results have been obtained with the selection of methacrylates (for example, polypropylene glycol monomethacrylate), as Component (E). In some aspects, Component (E) is selected from acrylates and methacrylates.

In some aspects, Component (E) is from about 0% to about 50% (by weight) of the silicone composition; alternatively from about 0% to about 30% (by weight) of the silicone composition; alternatively, from about 0% to about 5% (by weight) of the silicone composition.

Optional Component (F), Active Ingredient

Generally, optional Component (F) comprises at least one personal care or healthcare active ingredient that can be added to the silicone composition for in situ encapsulation by the elastomer particles. In some aspects, Component (F) may be added to the silicone composition during the making of the silicone elastomer (pre-load method) or may be added after formation of the silicone elastomer (post-load method). In some aspects, thermally-sensitive active ingredients are incorporated into the composition at temperatures below their threshold temperature for thermal response or decomposition. In some aspects, the active ingredient suspended in the gel can be, but is not required to be, in particulate form. When the active ingredient is in particulate form at the conditions of encapsulation, its particle size, distribution, or shape is not limited. By careful selection of the other components in the composition, the properties of the polymer particle may be controlled to allow a desirable mechanism of release of the active ingredient. Examples of release mechanisms include extraction, dissolution, swelling, melting, softening, degradation, abrading, squeezing or cracking via thermal, mechanical, or chemical or radiation-induced stress.

The amount of Component (F) present in the silicone composition may vary, but in some aspects ranges from about 0% to about 50% (by weight), alternatively from about 1% to about 25% (by weight), alternatively from about 1% to about 10% (by weight), based on the amount by total weight of components (A)-(E) in the silicone composition.

As used herein, a "personal care or healthcare active ingredient" means any compound or mixtures of compounds that are known in the art as additives in the personal care formulations that are typically added for the purpose of treating hair or skin to provide a cosmetic and/or aesthetic benefit; any compound or mixtures of compounds that are known in the art to provide a pharmaceutical or medical benefit; any compound that is intended to furnish pharmacological activity or other direct effect in the diagnosis, cure, mitigation, treatment, or prevention of disease, or to affect the structure or any function of the body of a human or other animals; and any compound that may undergo chemical change in the manufacture of drug products and be present in drug products in a modified form intended to furnish the specified activity or effect. Thus, "personal care and healthcare active ingredient" includes, but is not limited to, an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

Some representative examples of personal care and healthcare active ingredients include, but are not limited to, drugs; vitamins; proteins; fragrances or perfumes; plant extracts; minerals; hormones; topical antimicrobial agents such as antibiotic active ingredients; antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and sunburn prevention and treatment agents.

In some aspects, active ingredients suitable for Component (F) include both fat or oil-soluble vitamins, as well as water-soluble vitamins. Oil-soluble vitamins useful as Component (F) include, but are not limited to, Vitamin A1, RETINOL, $C_2$-$C_{18}$ esters of RETINOL, vitamin E, TOCOPHEROL, esters of vitamin E, and mixtures thereof. RETINOL includes trans-RETINOL, 1,3-cis-RETINOL, 11-cis-RETINOL, 9-cis-RETINOL, and 3,4-didehydro-RETINOL. It should be noted that RETINOL is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are RETINYL ACETATE, RETINYL PALMITATE, RETINYL PROPIONATE, a-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Water-soluble vitamins useful as Component (F) include, but are not limited to, Vitamin C, Vitamin B1, Vitamin B2, Vitamin B6, Vitamin B12, niacin, folic acid, biotin, and pantothenic acid. Other suitable water-soluble vitamins and the INCI names for the vitamins considered included herein are ASCORBYL DIPALMITATE, ASCORBYL METHYLSILANOL PECTINATE, ASCORBYL PALMITATE, and ASCORBYL STEARATE.

Some examples of commercially available products suitable for use as Component (F) are Vitamin A Acetate and Vitamin C, both products of Fluka Chemie AG, Buchs, Switzerland; COVI-OX T-50, a vitamin E product of Henkel Corporation, La Grange, Ill.; COVI-OX T-70, another vitamin E product of Henkel Corporation, La Grange, Ill.; and vitamin E Acetate, a product of Roche Vitamins & Fine Chemicals, Nutley, N.J.

In some aspects, the personal care or healthcare active ingredient used as Component (F) can be a water-soluble or an oil-soluble active drug ingredient. Representative examples of some suitable water-soluble active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, and mebendazole.

Representative examples of some suitable oil-soluble active drug ingredients which can be used as Component (F) are clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anaesthetic agents such as lidocaine; antipruritic agents; antidermatitis agents; and agents generally considered barrier films.

In some aspects, component (F) can also be a protein, such as an enzyme. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases and mixtures thereof.

In some aspects, component (F) may be a sunscreen agent. The sunscreen agent can be selected from any sunscreen agent known in the art to protect skin from the harmful effects of exposure to sunlight. The sunscreen can be an organic compound, an inorganic compound, or mixtures thereof. Thus, representative non limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate 0, Phenylbenzimidazole Sulfonic Acid, Red Petrolatum, Sulisobenzone, Titanium Dioxide, and Trolamine Salicylate.

The organic sunscreen compound is typically chosen from an organic compound that absorbs ultraviolet (UV) light. Some examples of UV light absorbing compounds are Acetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycin namate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, lsopropylbenzyl Salicylate, Isopropyl Dibenzolylmethane, isopropyl Methoxycinnamate, Menthyl Anthranilate, Menthyl Salicylate, 4-Methylbenzylidene Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, TriPABA Panthenol, Urocanic Acid, and VA/Crotonates/Methacryloxybenzophenone copolymer.

Alternatively, the sunscreen agent is a cinnamate based organic compound, or alternatively, the sunscreen agent is octyl methoxycinnamate, such as Uvinul® MC 80 an ester of para-methoxycinnamic acid and 2-ethylhexanol.

In some aspects, Component (F) may be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or sulphur containing compounds, as well as essential oils of natural or synthetic origin. Many of these perfume ingredients are described in detail in standard textbook references such as Perfume and Flavour Chemicals, 1969, S. Arctander, Montclair, N.J.

Fragrances may be exemplified by, but not limited to, perfume ketones and perfume aldehydes. Illustrative of the perfume ketones are buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-lonone, Beta-lonone, Gamma-Methyl so-called lonone, Fleuramone, Dihydrojasmone, Cis-Jasmone, lso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3, 5,5,-tetramethylCyclohexanone Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbornane, 6,7-Dihydro-1,1,2,3,3-Pentamethyl-4(5H)-lndanone 4-Damascol, Dulcinyl or Cassione, Gelsone, Hexylon, Isocyclemone E, Methyl Cyclocitrone, Methyl-Lavender-Ketone, Orivon, Para-tertiary-Butyl-Cyclohexanone, Verdone, Delphone, M uscone, Neobutenone, Plicatone, Veloutone, 2,4,4,7-Tetramethyl-oct-6-en-3-one, and Tetrameran.

More preferably, the perfume ketones are selected for its odour character from Alpha Damascone, Delta Damascone, Iso Damascone, Carvone, Gamma-Methyl-lonone, lso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odour character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cm namic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.O(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl) propanal, dihydrocinnamic aldehyde, 1-methyl-4-(4-methyl-3-pentenyl)-3-cyclohexene-1-carboxaldehyde, 5 or 6 methoxyl 0 hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyloctanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butena I, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-aI), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

More preferred aldehydes are selected for their odour character from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, hexanal, trans-2-hexenal, and mixture thereof.

In the above list of perfume ingredients, some are commercial names conventionally known to one skilled in the art, and also includes isomers. Such isomers are also suitable for use in the present invention.

In some aspects, Component (F) may be one or more plant extracts. Examples of these components are as follows: Ashitaba extract, avocado extract, hydrangea extract, Althea extract, Arnica extract, aloe extract, apricot extract, apricot kernel extract, Ginkgo Biloba extract, fennel extract, turmeric [Curcuma] extract, oolong tea extract, rose fruit extract, Echinacea extract, Scutellaria root extract, Phellodendro bark extract, Japanese Coptis extract. Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscustea extract, Pyracantha Fortuneana Fruit extract, Kiwi extract, Cinchona extract, cucumber extract, guanosine. Gardenia extract, Sasa Albo-marginata extract, Sophora root extract, Walnut extract, Grapefruit extract, Clematis extract, Chlorella extract, mulberry extract, Gentiana extract, black tea extract, yeast extract, burdock extract, rice bran ferment extract, rice germ oil, comfrey extract, collagen, cowberry extract, Gardenia extract, Asiasarum Root extract, Family of Bupleurum extract, Salvia extract, Saponaria extract, Bamboo extract, Crataegus fruit extract, Zanthoxylum fruit extract, shiitake extract, Rehmannia root extract, gromwell extract. Perilla extract, linden extract, Filipendula extract, peony extract, Calamus Root extract, white birch extract, Horsetail extract, Hedera Helix(Ivy) extract, hawthorn extract, Sambucus nigra extract, Achillea millefolium extract, Mentha piperita extract, sage extract, mallow extract, Cnidium officinale Root extract, Japanese green gentian extract, soybean extract, jujube extract, thyme extract, tea extract, clove extract, Gramineae imperata cyrillo extract, Citrus unshiu peel extract Japanese Angellica Root extract, Calendula extract, Peach Kernel extract, Bitter orange peel extract, Houttuyna cordata extract, tomato extract, natto extract, Ginseng extract, Green tea extract (camelliea sinesis), garlic extract, wild rose extract, hibiscus extract, Ophiopogon tuber extarct, Nelumbo nucifera extract, parsley extract, honey, hamamelis extract, Parietaria extract, Isodonis herba extract, bisabolol extract, Loquat extract, coltsfoot extract, butterbur extract, Porid cocos wolf extract, extract of butcher's broom, grape extract, propolis extract, luffa extract, safflower extract, peppermint extract, linden tree extract, Paeonia extract, hop extract, pine tree extract, horse chestnut extract, Mizu-bashou extract, Mukurossi peel extract, Melissa extract, peach extract, cornflower extract, eucalyptus extract, saxifrage extract, citron extract, coix extract, mugwort extract, lavender extract, apple extract, lettuce extract, lemon extract, Chinese milk vetch extract, rose extract, rosemary extract, Roman Chamomile extract, and royal jelly extract.

In some aspects, Component (F) is a personal care or health care active ingredient selected from vitamins, sunscreens, plant extracts, fragrances or perfumes, topical drug actives, proteins (including, but not limited to enzymes), antiperspirants, deodorants, moisturizers, antifungal agents, and antimicrobial agents.

Additional Optional Components

The silicone compositions can also include additional components. Without limitation, examples of such optional additional components include surfactants; emulsifiers; dispersants; polymeric stabilizers; crosslinking agents; combinations of polymers, crosslinking agents, and catalysts useful for providing a secondary polymerization or crosslinking of the particles; rheology modifiers such as thickeners; density modifiers; aziridine stabilizers; cure modifiers such as hydroquinone and hindered amines; free radical initiators such as organic peroxides and ozonides; polymers; diluents; acid acceptors; antioxidants; heat stabilizers; flame retardants; scavenging agents; silylating agents; foam stabilizers; solvents; diluents; plasticizers; fillers and inorganic particles, pigments, dyes and dessicants.

Compositions according to the invention may contain a number of optional components selected from those known in the state of the art to be ingredients in personal and healthcare formulations. Illustrative, non-limiting examples include surfactants, solvents, powders, coloring agents, thickeners, waxes, stabilizing agents, pH regulators, and silicones.

Thickening agents may optionally be added to the aqueous phase of the compositions to provide a convenient viscosity. For example, viscosities within the range of 500 to 25,000 mm$^2$/s at 25° C. or more, alternatively in the range of 3,000 to 7,000 mm$^2$/s at 25° C., are usually suitable. Suitable thickening agents are exemplified by sodium alginate; gum arabic; polyoxyethylene; guar gum; hydroxypropyl guar gum; ethoxylated alcohols, such as laureth-4 or polyethylene glycol 400; cellulose derivatives exemplified by methylcellulose, methylhydroxypropylcellulose, hydroxypropylcellulose, polypropylhydroxyethylcellulose; starch and starch derivatives exemplified by hydroxyethylamylose and starch amylose; locust bean gum; electrolytes exemplified by sodium chloride and ammonium chloride; saccharides such as fructose and glucose; and derivatives of saccharides such as PEG-120, methyl glucose diolate; or mixtures of two or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent may be present in shampoo compositions of the present invention in an amount sufficient to provide a viscosity in the final shampoo composition of from 500 to 25,000 mm$^2$/s. The thickening agent may be present in an amount from about 0.05 to 10 wt %; alternatively from about 0.05 to 5 wt %, based on the total weight of the composition. Thickeners based on acrylate derivatives, such as polyacrylate crosspolymer, Acrylates/C1030 Alkyl Acrylate crosspolymer, polyacrylamide derivatives, sodium polyacrylate may also be added.

Stabilizing agents may optionally be used in the water phase of compositions of the present invention. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to about 0.1 to 5 wt % and more alternatively 0.5 to 3 wt % of the total composition. The hydrocolloids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and Xantham gum.

Other optional components can include powders and pigments especially when the composition according to the invention is intended to be used for make-up. The powder component of the invention can be generally defined as dry, particulate matter having a particle size of 0.02-50 microns. The particulate matter may be colored or non-colored (for example white). Suitable powders include, but are not limited to, bismuth oxychloride, titanated mica, fumed silica, spherical silica beads, polymethylmethacrylate beads, boron nitride, aluminum silicate, aluminum starch octenylsuccinate, bentonite, kaolin, magnesium aluminum silicate, silica, silica silylate, talc, mica, titanium dioxide, nylon, silk powder. The above-mentioned powders may be surface treated to render the particles hydrophobic in nature. The powder component also comprises various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent colouring agent, such as carbon black, chromium or iron oxides, ultramarines, manganese pyrophosphate, iron blue, and titanium dioxide, pearlescent agents, generally used as a mixture with coloured pigments, or some organic dyes, generally used as a mixture with coloured pigments and commonly used in the cosmetics industry, can be added to the composition. In general, these colouring agents can be present in an amount by weight from 0 to 20% with respect to the weight of the final composition.

Pulverulent inorganic or organic fillers can also be added, generally in an amount by weight from 0 to 40% with respect to the weight of the final composition. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be crosslinked, copolymer microspheres such as EXPANCEL (Nobel Industrie), polytrap and silicone resin microbeads (TOSPEARL from Toshiba, for example).

Waxes or wax-like materials may be optional components of compositions of the present invention, wherein such components generally have a melting point range of 35 to 120° C. at atmospheric pressure. Waxes in this category include synthetic wax, ceresin, paraffin, ozokerite, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, soy waxes or mixtures thereof. Mention may be made, among the waxes capable of being used as non-silicone fatty substances, of animal waxes, such as beeswax; vegetable waxes, such as carnauba, candelilla wax, mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

Optional components may also include silicones (including any already described), organofunctional siloxanes, alkylmethylsiloxanes, siloxane resins and silicone gums. Alkylmethylsiloxanes useful for compositions of the present invention may have the formula Me$_3$SiO[Me$_2$SiO]$_y$[MeRSiO]$_z$SiMe$_3$, in which R is a hydrocarbon group containing 6-30 carbon atoms, Me represents methyl, and the degree of polymerization (DP), i.e., the sum of y and z is 3-50. Both the volatile and liquid species of alkymethysiloxanes can be used in the composition. Phenyl functional siloxanes may also be added such as Dow Corning® 556 Fluid.

Silicone gums may also be optional components of compositions of the present invention. Polydiorganosiloxane gums are known in the art and are available commercially. They consist of generally insoluble polydiorganosiloxanes having a viscosity in excess of 1,000,000 centistoke (mm²/s) at 25° C., alternatively greater than 5,000,000 centistoke (mm²/s) at 25° C. These silicone gums are typically sold as compositions already dispersed in a suitable solvent to facilitate their handling. Ultra-high viscosity silicones [those typically having a kinematic viscosity from about 5 million centistoke (mm²/s) at 25° C., to about 20 million centistoke (mm²/s) at 25° C.] can also be included as optional components. In some aspects, compositions of this type may be in the form of suspensions.

Silicone resins may also be optional components in compositions of the present invention. Such resins are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for use are generally supplied in an unhardened form in low viscosity volatile or nonvolatile silicone fluids, and may be incorporated into compositions of the present invention in their non-hardened forms rather than as hardened resinous structures.

Silicone carbinol fluids may also be optional components. These materials are described in WO 03/101,412 A2, and can be commonly described as substituted hydrocarbyl functional siloxane fluids or resins.

Water soluble or water dispersible silicone polyether compositions may also be optional components. These are also known as polyalkylene oxide silicone copolymers, silicone poly(oxyalkylene) copolymers, silicone glycol copolymers, or silicone surfactants. These can be linear rake or graft type materials, ABA or ABn type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible.

Compositions according to the present invention can be used in o/w, s/w, w/o, w/s, and non-aqueous o/o, o/s, and s/o emulsions or multiple phase emulsions using silicone emulsifiers. Typically the water-in-silicone emulsifier in such formulation is non-ionic and is selected from polyoxyalkylene-substituted silicones (rake or ABn type), silicone alkanolamides, silicone esters and silicone glycosides. Suitable silicone-based surfactants are well known in the art, and have been described for example in U.S. Pat. No. 4,122,029 (Gee et al.), U.S. Pat. No. 5,387,417 (Rentsch), and U.S. Pat. No. 5,811,487 (Schulz et al), JP 2001-294512.

When a composition according to the invention is an oil-in-water emulsion, it will include common ingredients generally used for preparing emulsions such as but not limited to non ionic surfactants well known in the art to prepare o/w emulsions. Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

The composition according to the invention can also be under the form of aerosols in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Methods

In various embodiments, provided are methods for the preparation of silicone elastomer compositions. Such methods comprise polymerizing Component (A) in the presence of Component (B), Component (C), and oxygen, and optionally Component (D), optionally Component (E), and optionally Component (F) while maintaining a temperature of from about 5° C. to about 95° C. to form a substantially homogenous silicone elastomeric gel. In some embodiments, the gel has an elastomer that is compatible with and absorbs Component (C). In some embodiments, the gel formed has a plateau elastic shear modulus not greater than one half of the intrinsic plateau elastic shear modulus of the silicone elastomer in its undiluted state.

In some embodiments, the method of preparing the gel comprises (I) forming a reaction mixture comprising Component (A), Component (B), Component (C), and optionally, one or more of Component (D), Component (E), or Component (F); (II) agitating the reaction mixture in the presence of oxygen; wherein agitation occurs during combination of the Components, after combination of the Components, or combinations thereof; and (III) allowing polymerization to continue until the gel is formed. In some aspects, one or more of Component (D), Component (E), or Component (F) may be added separately from Component (A), Component (B), and Component (C). For example, optional Component (F) may be added prior to polymerization of Component (A) (i.e. as part of the initial reaction mixture); during polymerization (i.e. during formation of the silicone elastomer); after polymerization [for example, during formation of the swollen gel by absorption of Component (C) by the elastomer]; or combinations thereof.

In some embodiments, agitation is continued until the gel composition is formed. In some embodiments, agitation occurs only to initiate the reaction and then is discontinued.

In some embodiments, agitation occurs in the presence of oxygen while maintaining the temperature at from about 5° C. to about 95° C. Thus, temperature may be from about 5° C. to about 10° C., from about 10° C. to about 15° C., from about 15° C. to about 20° C., from about 20° C. to about 25° C., from about 25° C. to about 30° C., from about 30° C. to about 35° C., from about 35° C. to about 40° C., from about 40° C. to about 45° C., from about 45° C. to about 50° C., from about 50° C. to about 55° C., from about 55° C. to about 60° C., from about 60° C. to about 65° C., from about 65° C. to about 70° C., from about 70° C. to about 75° C., from about 75° C. to about 80° C., from about 80° C. to about 85° C., from about 85° C. to about 90° C., and from about 90° C. to about 95° C. In some embodiments, agitation occurs in the presence of oxygen while maintaining the temperature at from about 10° C. to about 35° C. Thus, the temperature may be 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., and 35° C.

In some embodiments, a substantially homogenous swollen silicone gel composition prepared by the disclosed methods comprises Component (A), Component (B), Component (C), optionally Component (D), optionally Component (E), and optionally Component (F); or the reaction product(s) of two or more components. In some embodiments, a substantially homogenous swollen silicone gel composition prepared by the disclosed methods comprises the product formed by polymerizing Component (A) in the presence of Component (B), Component (C), oxygen, and optionally Component (D), optionally Component (E), and optionally Component (F).

In some embodiments, a silicone paste composition is prepared by shearing the silicone gel formed and optionally diluting with at least one miscible fluid, wherein the optional miscible fluid may be the same as Component (C), different from Component (C), or combinations thereof, but must be miscible with both the elastomer and Component (C) of the swollen silicone gel. In some embodiments, the paste formed comprises swollen silicone particles. In some embodiments, the optional miscible fluid may be selected from silicones, organic solvents and mixtures thereof. Suitable optional miscible fluids for use in diluting to form a silicone paste include, but are not limited to, linear and cyclosiloxanes, C8-C20 isoparaffins, esters and combinations thereof. For example, decamethylcyclopentasiloxane, isododecane, isohexadecane, or esters selected from isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-d isostearate, or mixtures thereof may be useful as the optional miscible fluid.

Silicone Gels, Powders, and Pastes

According to embodiments of the invention, provided are silicone compositions comprising an organopolysiloxane network, and methods of making such compositions. In some embodiments, the compositions are gels, pastes, or powders. In some embodiments, silicone gel compositions are prepared by a method comprising polymerizing organopolysiloxanes, via free radical polymerization initiated by organoborane free-radical catalysts, in the presence of at least one miscible fluid to form a silicone elastomeric matrix that absorbs the miscible fluid. Thus, the silicone gel compositions of the invention are homogenous (i.e. single phase), as the elastomer is swellable or otherwise compatible in the miscible fluid, and the miscible fluid becomes absorbed by the elastomer as it swells. In some embodiments, the composition comprises from about 20% to about 99% (by weight) of one or more miscible fluids, and from about 5% to about 80% (by weight) of elastomer. In some embodiments, the composition comprises from about 50% to about 90% (by weight) of one or more miscible fluids and from about 10% to about 50% (by weight) of elastomer. The miscible fluid is thickened by the resulting elastomeric matrix to form a gel or semi-solid state having a plateau elastic shear modulus (G) in the swollen state that is less than or equal to half the intrinsic plateau elastic shear modulus of the elastomer in its undiluted state.

In some embodiments, the silicone gel compositions comprise at least one personal or healthcare active ingredient. In some embodiments, such compositions are formed at room temperature to allow in situ incorporation of thermally-sensitive active ingredients into the elastomer particles. The active ingredient suspended in the gel can be, but is not required to be, in particulate form.

Silicone gel compositions of the present invention may be dried and pulverized to form a silicone powder. In some embodiments, the resulting microparticles are generally irregularly shaped, which is in contrast to methods in which microparticles are made directly by dispersion polymerization in a miscible fluid. Such silicone powders can be used in cosmetics and personal care and healthcare products, and since the powders can be formed from gel compositions comprising active ingredients, the powders are ideal for delivering active ingredients in products such as cosmetics, antiperspirants, deodorants, and moisturizers. In some embodiments, powders formed from the silicone gel compositions have an average particle size of from about 0.01 µm to about 2000 µm; alternatively, from about 0.1 µm to about 1000 µm. In some embodiments, the silicone powders comprise from about 5% to about 100% (by weight) of elastomer (100% obviously, if dried); alternatively, from about 25% to about 100% (by weight) of elastomer.

Silicone gel compositions of the present invention may also be used to form silicone pastes. Typically, a paste can be formed by applying high shear, cutting, abrasion, or impact to the gel either as it is being formed or after it is formed, preferably in the presence of a non-reactive diluent. In some embodiments, the non-reactive diluent is one or more miscible fluids that can be either the same as or different from the miscible fluid(s) used for formation of the gel [i.e. Component (C)]. Any type of mixing and shearing equipment, such as a batch mixer, planetary mixer, single or multiple screw extruder, dynamic or static mixer, colloid mill, ball mill, homogenizer, sonolator, or a combination thereof, may be used to apply shear force to the elastomeric gel. The application of shear, cutting, abrasion, or impact may be performed any temperature, including sub-ambient conditions such as found in cryo-milling or cryo-fracturing, room temperature, or elevated temperature. Good results have been obtained at temperatures at or below 40° C. In some embodiments, the silicone paste compositions comprise swollen non-spherical elastomeric particles. In some aspects, the silicone pastes comprise from about 5% to about 50% (by weight) of elastomer; alternatively, from about 10% to about 30% (by weight) of elastomer.

Pastes made from the swollen elastomeric gel compositions are stable and can have a wide range of viscosities, thereby making them particularly useful as bases for personal care and healthcare products. Such pastes are typically characterized as having high clarity, thixotropy, and shear thinning. In some embodiments, the silicone paste compositions have a viscosity of at least 25 Pa·s, alternatively at least 40 Pa·s, alternatively at least 100 Pa·s. In some embodiments, the pastes have a viscosity of from about 25 Pa·s to about 100 Pa·s. In some embodiments, the pastes have a viscosity of from about 25 Pa·s to about 40 Pa·s. In some embodiments, the pastes have a viscosity of from about 40 Pa·s to about 100 Pa·s. In some embodiments, the pastes have a viscosity greater than 100 Pa·s.

Personal Care and Healthcare Products

Silicone compositions are useful for a variety of applications. For example, they can be used for remediation or safe transport of non-polar fluids, such as fuels or oils; as a filler or insulation material for electrical cable; a soil or water barrier for in-ground stabilization; or as a replacement for epoxy materials used in coil-on-plug designs in the electronics industry. Such compositions can also be used as a carrier for crosslinked silicone rubber particles, allowing for ease of incorporation of particles into sealant, paint, coating, grease, adhesive, antifoam, and potting applications. Furthermore, silicone gel compositions can also be used as carriers for pharmaceuticals, biocides, pesticides, herbicides, and other biologically active substances, as well as for incorporating water and water-soluble substances, such as salicylic acid, glycerol, enzymes, and glycolic acid, into hydrophobic systems.

While applicable to purposes such as the aforementioned, silicone compositions of the present invention are particularly useful for personal care and healthcare products. For example, such compositions may be used in deodorants; antiperspirants; antiperspirant/deodorants; shaving products; skin care products such as lotions, moisturizers, and toners; bath products; cleansing products; hair care products such as shampoos, conditioners, mousses, styling gels, hair sprays, hair dyes, hair color products, hair bleaches, waving products, and hair straighteners; manicure products such as nail polish, nail polish remover, nail creams and lotions, and cuticle softeners; protective creams such as sunscreens, insect repellent and anti-aging products; cosmetics such as lipsticks, foundations, face powders, eye liners, eye shadows, blushes, makeup, mascaras; vitamin and hormone carriers; fragrance carriers; and other personal care formulations where silicone components have conventionally been added, as well as drug delivery systems for topical application of medicinal compositions that are to be applied to the skin.

For example, silicone compositions of the invention can be used to improve the properties of skin creams, skin care lotions, moisturizers, facial treatments such as ache or wrinkle removers, personal and facial cleansers, bath oils, perfumes, colognes, sachets, sunscreens, pre-shave and after-shave lotions, liquid soaps, shaving soaps, shaving lathers, hair shampoos, hair conditioners, hair sprays, mousses, permanents, depilatories, cuticle coats, and cosmetics. An example of their use in cosmetics is as leveling and spreading agents for pigments in make-ups, color cosmetics, foundations, blushes, lipsticks, lip balms, eyeliners, mascaras, oil removers, color cosmetic removers, and powders.

In various embodiments, silicone elastomeric gels, pastes, and powders of the present invention may be useful in personal care and healthcare products for humans or animals to moisturize, color, to generally improve appearance, or to apply active ingredients, such as sunscreens, deodorants, and insect repellents. For example, they may be useful as thickening agents, as taught in U.S. Pat. No. 6,051,216, U.S. Pat. No. 5,919,441, and U.S. Pat. No. 5,981,680; to structure oils, as disclosed in WO 2004/060271 and WO 2004/060101; in sunscreen compositions as taught in WO 2004/060276; as structuring agents in cosmetic compositions also containing film-forming resins, as disclosed in WO 03/105801; in the cosmetic compositions as taught in US2003/0235553, US2003/0072730, US2003/0170188, EP 1,266,647, EP 1,266,648, EP 1,266,653, WO 03/105789, WO 2004/000247, and WO 03/106614; as structuring agents as taught in WO 2004/054523; in long wearing cosmetic compositions as taught in US2004/0180032: in transparent or translucent care and/or make up compositions as discussed in WO 2004/054524; all of which are incorporated herein by reference.

Silicone elastomeric gels, pastes, and powders of the present invention may be useful in anti-perspirant and deodorant products including, but not limited to, in the form of sticks, soft solid, roll on, aerosol, and pump sprays. For example, such anti-perspirant and deodorant products may comprise as active ingredients, aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, and zinc ricinoleate.

Personal care and healthcare products of the present invention may be in the form of a cream, a gel, a powder, a paste, or a freely pourable liquid. Generally, such products can generally be prepared at room temperature if no solid materials at room temperature are present in the products, using simple propeller mixers, Brookfield counter-rotating mixers, or homogenizing mixers. No special equipment or processing conditions are typically required. Depending on the type of form made, the method of preparation will be different, but such methods are well known in the art.

Personal care and healthcare products of the present invention can be used by standard methods, such as applying them to the human body, e.g. skin or hair, using applicators, brushes, applying by hand, pouring them and/or possibly rubbing or massaging the products onto or into the body. Removal methods, for example for color cosmetics are also well known standard methods, including washing, wiping, and peeling. For use on the skin, personal care and healthcare products may be used in a conventional manner, for example for conditioning the skin. An effective amount of the product for the purpose is applied to the skin. Such effective amounts generally range from about 1 mg/cm$^2$ to about 3 mg/cm$^2$. Application to the skin typically includes working the composition into the skin. This method for applying to the skin comprises the steps of contacting the skin with the product in an effective amount and then rubbing the product into the skin. These steps can be repeated as many times as desired to achieve the desired benefit.

For use on hair, personal care and healthcare products may be used in a conventional manner, for example for conditioning hair. An effective amount of the product for the purpose is applied to the hair. Such effective amounts generally range from about 1 g to about 50 g, alternatively from about 1 g to about 20 g. Application to the hair typically includes working the product through the hair such that most or all of the hair is contacted with the product. This method for applying to the hair comprises the steps of contacting the hair with the product in an effective amount and then working the product through the hair. These steps can be repeated as many times as desired to achieve the desired benefit.

In some embodiments, personal care and healthcare products of the present invention are selected from antiperspirants, deodorants, skin creams, skin care lotions, moisturizers, facial treatment products, facial cleansing products, bath oils, perfumes, colognes, sachets, sunscreens, pre-shave lotions, after-shave lotions, liquid soaps, body washes, bar soaps, shaving soaps, shaving lathers, hair shampoos, hair conditioners, hair colorants, hair sprays, mousses, permanents, depilatories, cuticle coats, make-ups, color cosmetics, foundations, blushes lipsticks, lip balms, eyeliners, mascaras, eye shadows, oil removers, and cosmetic removers.

EXAMPLES

The present invention will be better understood by reference to the following examples which are offered by way of illustration and which one of skill in the art will recognize are not meant to be limiting.

Example 1

Method of Making a Swollen Elastomer

The following procedure was followed (with substitution of materials as listed in Table 1) to create silicone gels having swollen elastomers. All steps were completed under ambient laboratory temperature.

1. The following components were mixed for 20 seconds in a Max 20 Speedmixer cup to form Mixture A: 3.53 g of a 4.3 wt % solution of Component (B), TNBB-MOPA (tri-n-butyl borane complexed with 1.3 molar equivalents of 3-methoxypropyl amine) in Component (A), MA-PDMS (methacryloxypropyldimethylsiloxy-terminated polydimethylsiloxane having a number average molecular weight of 8,000 g/mol) and 16.52 g of Component (C), decamethylcyclopentasiloxane (D5).
2. The following materials were mixed for 20 seconds in a second Max 20 Speedmixer cup to form Mixture B: 3.51 g of a 4.3 wt % solution of Component (D) in Component (A), MA-PDMS and 16.61 g of Component (C), decamethylcyclopentasiloxane.
3. 19.41 g of Mixture B were added to 19.19 g of Mixture A in an 8 ounce glass jar containing a magnetic stir bar that was continuously stirred with a magnetic stirrer in a nitrogen purged atmosphere.
4. The material was allowed to continue mixing until the material became too viscous (cured) for the stir bar to continue and formed a swollen elastomer. This curing happened after approximately 30 minutes.
5. As needed, additional D5 (or substitute miscible fluid) was added to achieve the desired final elastomer content (FEC).

Example 2

Method of Making an Elastomer Paste of Swollen Non-Spherical Elastomeric Particles The following procedure was followed to create elastomer pastes of swollen non-spherical elastomeric particles described in Example 1, but with the appropriate substitution of materials & quantities described.

1. 12.97 g of the swollen elastomer from Comp. E (Example 1) was placed into a Max 20 Speedmixer cup.
2. Approximately 1 to 2 grams of dry ice were added to the Max 20 Speedmixer cup which had a small hole drilled into the lid to relieve pressure from any evaporation of the dry ice. The container was mixed for two 30 second cycles with an intermediate spatula mixing cycle.
3. Step 2 was repeated until visual inspection of the blend indicated a reduced particle size.
4. After particle size reduction, the sample was further diluted with additional D5 to the desired final elastomer content (FEC). 5.40 g D5 was added incrementally with mixing in between. This gave a final elastomer content of 12.4%.
5. The resulting Elastomer paste had a $\eta'$ value of 48.5 Pa·s measured at 10 rad/s at 5% strain.

Example 3

Rheological Testing of Modulus

Modulus measurements of samples were obtained in frequency sweep mode using the parallel plate geometry on a Rheometrics Dynamic Analyzer RDA II rheometer. Moduli

TABLE 1

| Composition | MA-PDMS (g) | TnBB-MOPA (g) | ON-RC | ON-RC (g) | Diluent | Diluent (g) | % IEC | % FEC | APTES (g) | % APTES |
|---|---|---|---|---|---|---|---|---|---|---|
| A | 20.13 | 0.54 | IPDI | 0.43 | NA | 0.00 | 100.0% | 100.0% | | |
| B | 3.34 | 0.09 | IPDI | 0.07 | D5 | 16.55 | 17.5% | 17.5% | | |
| C | 1.41 | 0.04 | IPDI | 0.03 | D5 | 7.03 | 17.4% | 17.4% | | |
| D | 1.81 | 0.05 | IPDI | 0.04 | D5 | 12.67 | 13.0% | 13.0% | | |
| E | 6.47 | 0.14 | IPDI | 0.15 | D5 | 31.84 | 17.5% | 17.5% | | |
| F | 2.17 | 0.05 | IPDI | 0.05 | D5 | 16.10 | 17.5% | 12.4% | | |
| G | 1.02 | 0.02 | IPDI | 0.02 | D5 | 13.94 | 17.5% | 7.1% | | |
| H | 3.39 | 0.08 | Acetic Acid | 0.03 | NA | 0.00 | 100.0% | 100.0% | | |
| I | 9.10 | 0.21 | Acetic Acid | 0.09 | D5 | 9.09 | 50.8% | 50.8% | | |
| J | 3.20 | 0.08 | Acetic Acid | 0.04 | D5 | 15.61 | 17.5% | 17.5% | | |
| K | 2.92 | 0.08 | COOH-PDMS | 0.35 | D5 | 15.83 | 17.4% | 17.4% | | |
| L | 4.66 | 0.11 | Acetic Acid | 0.05 | IDD | 14.40 | 25.1% | 25.1% | | |
| M | 5.21 | 0.12 | IPDI | 0.12 | D5 | 5.45 | 50.0% | 50.0% | | |
| N | 3.18 | 0.07 | IPDI | 0.08 | D5 | 16.42 | 16.8% | 16.8% | | |
| O | 15.53 | 0.35 | Acetic Acid | 0.14 | NA | 0.00 | 100.0% | 100.0% | | |
| P | 0.67 | 0.02 | Acetic Acid | 0.01 | D5 | 3.32 | 17.3% | 17.3% | 0.02 | 0.5% |
| Q | 0.79 | 0.02 | Acetic Acid | 0.01 | D5 | 3.20 | 20.3% | 20.3% | 0.05 | 1.3% |

ON-RC = organonitrogen-reactive compound
IPDI = isophorone diisocyanate
D5 = decamethylcyclopentasiloxane
IDD = isododecane
APTES = 3-aminopropyltriethoxysilane reported are dynamic storage moduli (G') at 5% strain and a frequency of 10 rad/s. This value was selected as most representative of the plateau in G' that is associated with elastomeric materials. Sample thicknesses typically ranged between 1-3 mm. Data gathered during the analysis were processed using TA Orchestrator Version V7.1.2.3. All tests were performed at room temperature.

Figure 1:
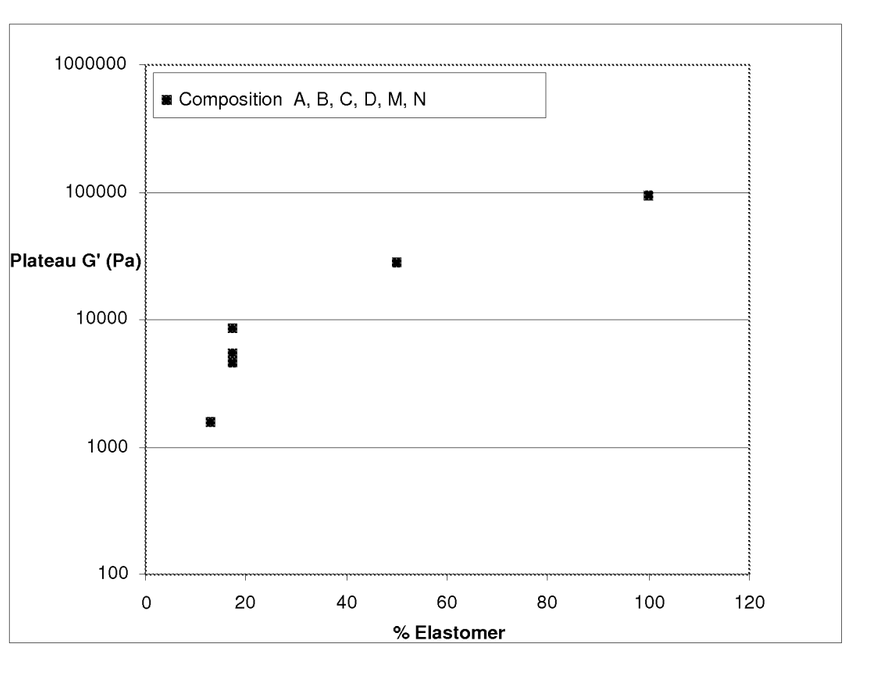
FIG. 1 illustrates rheological testing of various gel compositions (Example 3), wherein plateau shear modulus is plotted as a function of final elastomer content (FEC).

Sample compositions from Example 1 were measured, and the data is shown in Table 2 and is plotted in FIG. 1 as a function of FEC. Comparison of Comp. No. R and Comp. No. A show that approximately 50% or greater reduction in G' can be obtained by diluting a cured sample in additional solvent. Hence, the modulus of the materials of this invention may be adjusted by additional dilution or removal of solvent.

TABLE 2

| Composition | IEC (%) | FEC (%) | Plateau G' (Pa) |
|---|---|---|---|
| A | 100 | 100 | 9.2E+04 |
| B | 17.4 | 17.4 | 8.5E+03 |
| C | 17.4 | 17.4 | 5.4E+03 |
| D | 13.0 | 13.0 | 1.6E+03 |
| M | 50.0 | 50.0 | 3.8E+04 |
| N | 17.5 | 17.5 | 4.5E+03 |
| R | 100.0 | 48.1 | 2.4E+04 |
| S | 17.4 | 12.0 | 2.0E+03 |

Example 4

Anti-Perspirant

The following ingredients were added to an empty Max 20 Hauschild cup: (i) 3.79 g elastomer paste of Comp. No. S; (ii) 0.30 g C12-15 Alkyl Benzoate (Finsolv TN); (iii) 2.506 g Aluminum-Zirconium Tetrachlorohydren-Gly, USP (Summit AAZG-7167); (iv) 0.10 g Silicone Elastomer Powder (9506 Powder); and (v) 3.36 g Mixture of Dimethicone and Trisiloxane (2-1184). The ingredients were mixed in a Hauschild mixer at the maximum speed for a period of 30 s. With a spatula, the sample material was carefully mixed in the cup, taking care to ensure that material from sides and bottom become uniformly incorporated. The material was again mixed in the Hauschild mixer at maximum speed for 30 s. The resulting material was visually checked for uniform appearance.

Example 5

Facial Moisturizer

A facial moisturizer was prepared as follows. Mixture A was formed by combining: (i) 1.01 g Elastomer paste (Comp. No. S diluted in D5 to 7% FEC); (ii) 0.52 g Octyl Methoxycinnamate; and (iii) 0.33 g Polyacrylamide (and) C13-14 Isoparaffin (and) Laureth-7 (Sepigel 305) in a Hauschild mixer for 30 s. Mixture B was formed by combining: (i) 0.40 g Glycerol; (ii) 0.04 g DMDM Hydantoin; and (iii) 7.84 g DI Water in a Hauschild mixer for 30 s. Mixture A and Mixture B were combined and mixed in a Hauschild mixer for 30 s.

Example 6

Gelled Solvent Comprising Hydrophilically Modified Silicone Elastomer

The following procedure was followed to create swollen elastomer. All steps were completed under ambient laboratory temperature.

1. Mixture A was prepared by mixing for 20 s in a Max 10 Speedmixer cup: 1.21 g of a 4 wt % solution of TNBB-MOPA in MA-PDMS and 4.80 g D5.
2. Mixture B was prepared by mixing for 20 s in a second Max 10 Speedmixer cup: 1.21 g of a 4 wt % IPDI and 10 wt % solution of Polypropylene glycol monomethacrylate in MA-PDMS and 4.80 g D5.
3. 5.61 g of Mixture B were added to 5.69 g of Mixture A in an 8 ounce glass jar containing a magnetic stir bar that was continuously stirred with a magnetic stirrer in a nitrogen purged atmosphere.
4. The material was allowed to continue mixing until the material became too viscous (cured) for the stir bar to continue and formed a swollen elastomer. This curing happened after approximately 35 minutes.
5. 2.41 g additional D5 was added to 4.51 g of the swollen elastomer to achieve the desired final elastomer content (FEC) of 13%. The method of Example 2 was used to produce a paste of these non-spherical elastomeric particles. The final result was a gelled solvent.

The present invention should not be considered limited to the specific examples described herein, but rather should be understood to cover all aspects of the invention. Various modifications and equivalent processes, as well as numerous structures and devices, to which the present invention may be applicable will be readily apparent to those of skill in the art. Those skilled in the art will understand that various changes may be made without departing from the scope of the invention, which is not to be considered limited to what is described in the specification.

The invention claimed is:

1. A method for the preparation of a silicone composition, the method comprising:
    combining
        Component (A), at least one organopolysiloxane having an average of at least two free radical polymerizable groups per molecule, the organopolysiloxane having the structure:

wherein
            at each occurrence $R^1$ and $R^3$ are independently chosen from halogen and a monovalent organic group,
            at each occurrence $R^2$ and $R^4$ are independently a monovalent unsaturated organic group,
            a, c, and d are independently about 0 to about 20,000, and b is about 1 to about 20,000,
        Component (B), at least one organoborane free radical initiator, and
        Component (C), at least one fluid miscible with Component (A), to form a reaction mixture, wherein Component (B) is the only catalyst present in the reaction mixture; and
    gelling the reaction mixture to form a substantially homogeneous swollen silicone gel, the gelling comprising
        polymerizing Component (A) in the presence of Component (B), Component (C), and oxygen, while maintaining a temperature of from about 5° C. to about 95° C., to form the substantially homogeneous swollen silicone gel, wherein about 50 wt % to about 90 wt % of the substantially homogeneously swollen silicone gel is Component (C).

2. The method according to claim 1, wherein the polymerizing comprises maintaining the temperature at from about 10° C. to about 35° C. and wherein the swollen silicone gel has a plateau elastic shear modulus not greater than one half of an intrinsic plateau elastic shear modulus of an elastomer component of the swollen silicone gel in an undiluted state.

3. The method according to claim 2, comprising shearing the swollen silicone gel and optionally diluting it with at least one miscible fluid that is compatible with the elastomer component and Component (C) to form a silicone paste comprising swollen silicone microparticles; wherein the optional miscible fluid is the same as Component (C), different from Component (C), and any combination thereof.

4. The method according to claim 3, further including diluting the swollen silicone gel with at least one miscible fluid, the at least one miscible fluid being selected from silicones.

5. The method according to claim 1, wherein Component (A) is selected from acrylate and methacrylate-functional polydimethylsiloxanes and resins.

6. The method according to claim 1, wherein Component (B) is a trialkylborane-organonitrogen complex wherein the trialkylborane is selected from triethylborane, tri-n-butylborane, tri-n-octylborane, tri-sec-butylborane, tridodecylborane, and any combination thereof.

7. The method according to claim 1, wherein polymerization occurs in the presence of Component (D), at least one organonitrogen-reactive compound selected from isophorone diisocyanate, acetic acid, carboxyl-terminated polydimethylsiloxane, and any combination thereof.

8. The method according to claim 1, wherein polymerization occurs in the presence of Component (E), at least one free-radical polymerizable organic co-monomers selected from acrylates, methacrylates, and any combination thereof.

9. The method according to claim 1, wherein polymerization occurs in the presence of, or the silicone gel formed is treated with Component (F), at least one active ingredient suitable for use in personal care and healthcare products.

10. The method according to claim 3, further including diluting the swollen silicone gel with at least one miscible fluid, the at least one miscible fluid being selected from linear and cyclosiloxanes, and combinations thereof.

11. The method according to claim 10, wherein the at least one miscible fluid is a cyclosiloxane, the cyclosiloxane being decamethylcyclopentasiloxane.

12. The method according to claim 3, further including diluting the swollen silicone gel with at least one miscible fluid, the at least one miscible fluid being an organic solvent or a combination thereof.

13. The method according to claim 3, further including diluting the swollen silicone gel with at least one miscible fluid, the at least one miscible fluid being an ester or a combination thereof.

14. The method according to claim 5, wherein Component (A) is selected from methacryloxypropyldimethylsiloxy-terminated polydimethylsiloxane, methacryloxymethylsiloxy-terminated polydimethylsiloxanes, acryloxypropyldimethylsiloxy-terminated polydimethylsiloxanes, acryloxymethyldimethylsiloxy-terminated polydimethylsiloxanes, polydimethylsiloxane-polymethyl-methacryloxypropylsiloxane copolymers, polydimethylsiloxane-polymethyl-acryloxypropylsiloxane copolymers, and any combination thereof.

* * * * *